United States Patent
Guevremont

(10) Patent No.: US 6,987,262 B2
(45) Date of Patent: Jan. 17, 2006

(54) FAIMS APPARATUS AND METHOD FOR DETECTING TRACE AMOUNTS OF A VAPOUR IN A CARRIER GAS

(75) Inventor: Roger Guevremont, Ottawa (CA)

(73) Assignee: Ionalytics Corporation, Ottawa (CA)

( * ) Notice: Subject to any disclaimer, the term of this patent is extended or adjusted under 35 U.S.C. 154(b) by 0 days.

(21) Appl. No.: 10/503,657

(22) PCT Filed: Feb. 7, 2003

(86) PCT No.: PCT/CA03/00172

§ 371 (c)(1),
(2), (4) Date: Aug. 6, 2004

(87) PCT Pub. No.: WO03/067242

PCT Pub. Date: Aug. 14, 2003

(65) Prior Publication Data

US 2005/0116160 A1    Jun. 2, 2005

Related U.S. Application Data

(60) Provisional application No. 60/345,345, filed on Jan. 4, 2002.

(51) Int. Cl.
*H01J 49/40* (2006.01)
(52) U.S. Cl. ............... 250/288; 250/286; 250/281; 250/282
(58) Field of Classification Search ........ 250/288, 250/286, 281, 282
See application file for complete search history.

(56) References Cited

U.S. PATENT DOCUMENTS 3,668,383 A    6/1972    Carroll

| 4,311,669 A | 1/1982 | Spangler |
| 5,106,468 A | 4/1992 | Chimenti |
| 5,283,199 A | 2/1994 | Bacon et al. |

(Continued)

FOREIGN PATENT DOCUMENTS

RU    2105298    2/1998

OTHER PUBLICATIONS

Mason et al., "Transport Properties of Ions in Gases", (1988), Wiley, New York.

(Continued)

*Primary Examiner*—Nikita Wells
(74) *Attorney, Agent, or Firm*—Freedman & Associates

(57) ABSTRACT

Disclosed is a method and apparatus for detecting trace levels of a vapour in a carrier gas stream. A method according to the instant invention comprises the steps of providing a flow of a carrier gas through an analyzer region of a high field asymmetric waveform ion mobility spectrometer (22), the carrier gas including a first gas and a trace amount of a vapour. At least a first type of indicator ions are introduced into the analyzer region, and a compensation voltage for transmitting the at least a first type of indicator ions through the analyzer region, in the presence of the flow of a carrier gas and at a given asymmetric waveform voltage, is determined. The determined compensation voltage is compared to calibration data relating to a compensation voltage for transmitting the at least a first type of indicator ions through the analyzer region at the given asymmetric waveform voltage in the presence of each of a plurality of different known trace amounts of the vapour mixed with the first gas. In this way, an amount of the vapour in the carrier gas is determined, absent a step of ionizing a substantial portion of the vapour.

43 Claims, 13 Drawing Sheets

U.S. PATENT DOCUMENTS

| | | | |
|---|---|---|---|
| 5,420,424 | A | 5/1995 | Carnahan et al. |
| 5,455,417 | A | 10/1995 | Sacristan |
| 5,723,861 | A | 3/1998 | Carnahan et al. |
| 5,736,739 | A | 4/1998 | Uber et al. |
| 5,763,876 | A | 6/1998 | Pertinarides et al. |
| 5,869,831 | A | 2/1999 | De La Mora et al. |
| 6,495,823 | B1 | 12/2002 | Miller et al. |
| 6,504,149 | B2 * | 1/2003 | Guevremont et al. ....... 250/286 |
| 6,512,224 | B1 | 1/2003 | Miller et al. |
| 6,559,441 | B2 | 5/2003 | Clemmer |
| 6,621,077 | B1 | 9/2003 | Guevremont et al. |
| 6,639,212 | B1 * | 10/2003 | Guevremont et al. ....... 250/282 |
| 6,690,004 | B2 | 2/2004 | Miller et al. |
| 6,774,360 | B2 * | 8/2004 | Guevremont et al. ....... 250/288 |
| 2003/0057369 | A1 | 3/2003 | Guevremont et al. |
| 2005/0151072 | A1 * | 7/2005 | Guevremont et al. ....... 250/282 |

OTHER PUBLICATIONS

Buryakov et al., "A New Method of Seperation of Multi-Atomic Ions by Mobility at Atmospheric Pressure using a High-Frequency Amplitude-Asymmetric Strong Electric Field", Int. J. Mass Spectrom. Ion Processes, No. 128, pp. 143-148, (1993), Elsevier Science Publishers B.V.

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96-009, pp. 87-95, (1996), Framingham, MA, USA.

Guevremont et al., "Combined Ion Mobility/Time-of-Flight Mass Spectrometry Study of Electrospray-Generated Ions", Anal. Chem. 1997, vol. 69, No. 19, pp. 3959-3965, (Oct. 1, 1997), American Chemical Society.

Hudgins et al., "High Resolution Ion Mobility Measurments for Gas Phase Proteins: Correlation beteen Solution Phase and Gas Phase Conformations", Int. J. of Mass Spec. and Ion Processes 165/166, pp. 497-507, (1997), Elsevier Science Publishers B. V.

Riegner et al., "Qualitative Evaluation of Field Ion Spectrometry for Chemical Warfare Agent Detection", Proceedings of the 45th ASMS Conference on Mass Spectrometry and Allied Topics, Palm Springs, California, pp. 473, (1997).

Purves et al., "Mass Spectrometric Characterization of a High-Field Asymmetric Waveform Ion Mobility Spectrometer", Review of Scientific Instruments, vol.69, No. 12, pp. 4094-4105, (Dec. 1998), American Institute of Physics.

Henderson et al., "ESI/Ion Trap/Ion Mobility/Time-of-Flight Mass Spectrometry for Rapid and Sensitive Analysis of Biomolecular Mixtures", Anal. Chem. 1999, vol. 71, No. 2, pp. 291-301, (Jan. 15, 1999), American Chemical Society.

Guevremont et al., "Atmospheric Pressure Ion Focusing in a High-Field Asymmetric Waveform Ion Mobility Spectrometer", Review of Scientific Instruments, vol. 70, No. 2, pp. 1370-1\383, (Feb. 1999), American Institute of Physics.

Purves et al., "Elongated conformers of charge states +11 to +15 of bovine ubiquitin studied using ESI-FAIMS-MS", J.Am.Soc.Mass.Spectrom., vol. 12, No. 8, Aug. 2001, pp. 894-901, Elsevier Science Inc., New York, NY, US.

* cited by examiner

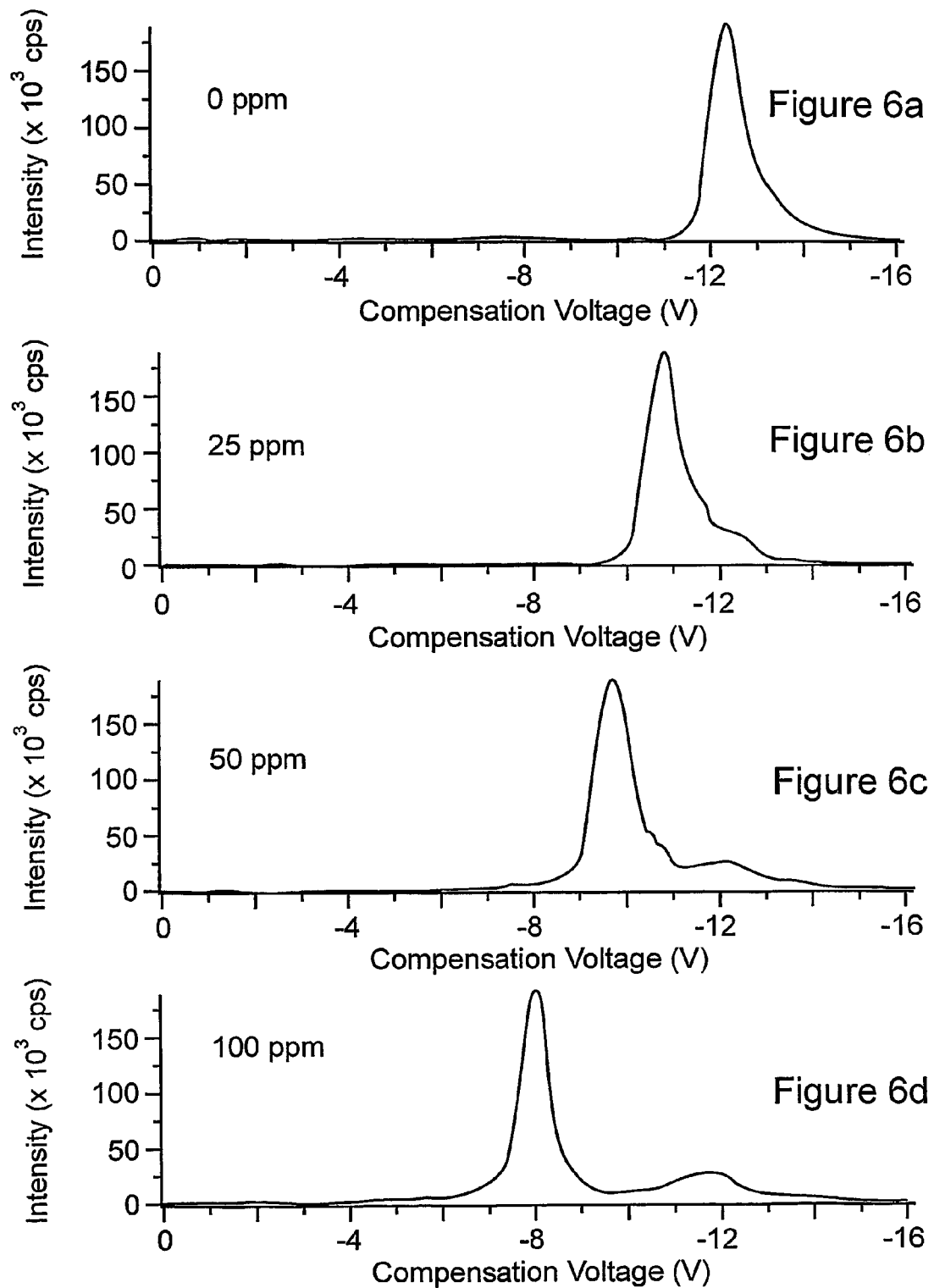

US 6,987,262 B2

FAIMS APPARATUS AND METHOD FOR DETECTING TRACE AMOUNTS OF A VAPOUR IN A CARRIER GAS

This application claims the benefit of U.S. Provisional Application No. 60/354,711, filed Feb. 8, 2002.

FIELD OF THE INVENTION

The instant invention relates generally to high field asymmetric waveform ion mobility spectrometry (FAIMS), more particularly the instant invention relates to an apparatus and a method for using indicator ions to indirectly detect trace amounts of a vapour in a carrier gas.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 $\mu$s followed by −1000 V for 20 $\mu$s. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = V_H t_H = K_H E_H t_H$, where $t_H$ is the time period of the applied high voltage. During the longer duration, opposite polarity, low voltage portion of the asymmetric waveform, the y-axis velocity component of the ion is $V_L = K E_L$, where K is the low field ion mobility under operating pressure and temperature conditions. The distance traveled is $d_L = V_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

U.S. Pat. No. 5,420,424, issued to Carnahan and Tarassov on May 30, 1995, teaches a FAIMS device having cylindrical electrode geometry and electrometric ion detection, the contents of which are incorporated herein by reference. The FAIMS analyzer region is defined by an annular space between inner and outer cylindrical electrodes. In use, ions that are to be separated are entrained into a flow of a carrier gas and are carried into the analyzer region via an ion inlet orifice. Once inside the analyzer region, the ions become distributed all the way around the inner electrode as a result of the carrier gas flow and ion-ion repulsive forces. The ions are selectively transmitted within the analyzer region to an ion extraction region at an end of the analyzer region opposite the ion inlet end. In particular, a plurality of ion outlet orifices is provided around the circumference of the outer electrode for extracting the selectively transmitted ions from the ion extraction region for electrometric detection. Of course, the electrometric detectors provide a signal that is indicative of the total ion current arriving at the detector. Accordingly, the CV spectrum that is obtained using the Carnahan device does not include information relating to an identity of the selectively transmitted ions. It is a limitation of the Carnahan device that the peaks in the CV spectrum are highly susceptible to being assigned incorrectly.

Replacing the electrometric detector with a mass spectrometer detection system provides an opportunity to obtain additional experimental data relating to the identity of ions giving rise to the peaks in a CV spectrum. For instance, the mass-to-charge (m/z) ratio of ions that are selectively transmitted through the FAIMS at a particular combination of CV and DV can be measured. Additionally, replacing the mass spectrometer with a tandem mass spectrometer makes it possible to perform a full-fledged structural investigation of the selectively transmitted ions. Unfortunately, the selectively transmitted ions are difficult to extract from the analyzer region of the Carnahan device for subsequent detection by a mass spectrometer. In particular, the orifice plate of a mass spectrometer typically includes a single small sampling orifice for receiving ions for introduction into the mass spectrometer. This restriction is due to the fact that a mass spectrometer operates at a much lower pressure than the FAIMS analyzer. In general, the size of the sampling orifice into the mass spectrometer is limited by the pumping efficiency of the mass spectrometer vacuum system. In principle, it is possible to align the sampling orifice of a mass spectrometer with a single opening in the FAIMS outer electrode of the Carnahan device; however, such a combination suffers from very low ion transmission efficiency and therefore poor detection limits. In particular, the Carnahan device does not allow the selectively transmitted ions to be concentrated for extraction through the single opening. Accordingly, only a small fraction of the selectively transmitted ions are extracted from the analyzer region, the vast majority of the selectively transmitted ions being neutralized eventually upon impact with an electrode surface.

Guevremont et al. describe the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region between the cylindrical electrodes as a result of the electric fields which change with radial distance. Focusing the ions of interest has the effect of reducing the number of ions of interest that are lost as a result of the ion suffering a collision with one of the inner and outer electrodes.

In WO 00/08455, the contents of which are incorporated herein by reference, Guevremont and Purves describe a domed-FAIMS analyzer. In particular, the domed-FAIMS analyzer includes a cylindrical inner electrode having a curved surface terminus proximate the ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, except that the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ion cloud to travel towards the ion-outlet orifice, which advantageously also prevents the ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned domed-FAIMS device, which can be used to achieve ion transmission from the domed-FAIMS to an external mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions are extracted from this region as a narrow, approximately collimated beam, which is pulled by the gas flow through the ion-outlet orifice and into a smaller orifice leading into the vacuum system of the mass spectrometer. Accordingly, such tandem FAIMS/MS devices are highly sensitive instruments that are capable of detecting and identifying ions of interest at part-per-billion levels.

Prior art FAIMS devices typically use a carrier gas comprising a purified flow of one of nitrogen, oxygen and air. However, in some cases there are very significant deviations from the predicted and obvious behavior of ions in mixtures of gases. These deviations have major implications on the application of FAIMS, since in some cases the use of a mixture of gases will make separations of certain ions feasible, where the separation is other than possible with the normal selection of pure gases. In WO 01/69646, the contents of which are herein incorporated by reference, Guevremont et al. describe in detail the effect of using gas mixtures to change the separation capabilities and signal intensity of ions transmitted through a FAIMS device. The behavior of ions in these gas mixtures is not predictable based on the behavior of the ions in the individual gases in the mixture. It was speculated that in some cases, the ion formed complexes with an added gas, such as for example carbon dioxide, and that the complexes re-formed and dissociated during application of the asymmetric waveform, thus greatly amplifying the velocity difference of the ions as they traveled in the high and low field periods of the waveform. This unexpected behavior led to unforseen advantages for the analyses of several ions using a FAIMS device. However, for these gas mixtures, the amount of each gas used to induce changes was always >1%.

It has now been discovered that an addition of a trace amount of a so called "magic bullet" vapour, for example levels in the ppm range or lower, promotes significant changes in the behavior of selected "target" ions in a FAIMS device. The observed sensitivity of some of the analyte ions to trace amounts of these vapours enables a new method for detection of these vapours.

Several trace analytical instrumental methods have been reported for detecting compounds at trace levels in a gas mixture, including mass spectrometry and ion mobility spectrometry. These prior art methods, especially the extremely sensitive methods of mass spectrometry and ion mobility spectrometry, require that the compound of interest be ionized in order for the compound to be separated from other ionic species that were formed from the sample, and for the species to be detected. The sample is analyzed using a procedure that usually provides a mechanism, for example proton transfer reactions, to form ionic species, including use of radioactivity, ultraviolet radiation, and corona discharge ionization. Following ionization, the ion of interest must be separated from coexisting ions from other compounds and contaminants in the gas, and finally the ion must be detected. The instrumentation to carry out these procedures is well known in the analytical chemistry literature. All of these well-known procedures fail if the compound of interest does not form an ionic species. Failure to form an ion may result from several of the properties of the compound of interest. For example, hydrocarbon compounds do not form ions using conventional atmospheric pressure radioactivity or corona discharge methods, because other compounds including the bath gas generally have a higher affinity for protons than does the hydrocarbon compound.

It would be advantageous to provide a method of detecting trace levels of vapours in a gas that overcomes the limitations of the prior art.

SUMMARY OF THE INVENTION

In accordance with an aspect of the instant invention there is provided a method of detecting trace levels of a vapour in a carrier gas, comprising the steps of: providing a flow of a carrier gas through an analyzer region of a high field asymmetric waveform ion mobility spectrometer, the carrier gas including a first gas and a trace amount of a vapour; introducing a first type of indicator ions into the analyzer region; determining a compensation voltage for transmitting the first type of indicator ions through the analyzer region in the presence of the flow of a carrier gas and at a given asymmetric waveform voltage; and, comparing the determined compensation voltage to calibration data relating to a compensation voltage for transmitting the first type of indicator ions through the analyzer region at the given asymmetric waveform voltage in the presence of each of a plurality of different known trace amounts of the vapour mixed with the first gas.

In accordance with another aspect of the instant invention there is provided a method of detecting trace levels of a vapour in a carrier gas, comprising the steps of: providing a flow of a carrier gas through an analyzer region of a high field asymmetric waveform ion mobility spectrometer, the carrier gas including a trace amount of a vapour of a compound of interest; introducing indicator ions into the analyzer region; transmitting the indicator ions through the analyzer region at a given combination of an asymmetric waveform voltage and a compensation voltage; and, determining a value relating to a concentration of the vapour based upon a comparison of the compensation voltage for transmitting the indicator ions to calibration data relating to compensation voltage values for transmitting the indicator ions at a same asymmetric waveform voltage for each of a plurality of different known amounts of the vapour, whereby the vapour of the compound of interest is substantially other than ionized.

In accordance with still another aspect of the instant invention there is provided an apparatus for detecting trace levels of a vapour in a carrier gas comprising: a gas source for providing a flow of a carrier gas including a trace amount of a vapour of interest; an analyzer region defined by a space between two spaced-apart electrodes, the analyzer region having an inlet at a first end and an outlet at a second end for providing, in use, a flow of the carrier gas including a trace amount of the vapour of interest through the analyzer region; an ionization source disposed adjacent to the inlet of the analyzer region for producing indicator ions from at least a sample containing indicator ion precursors and for introducing the indicator ions through the inlet and into the analyzer region; and, a power supply connectable to at least one of the two electrodes and capable of applying an asymmetric waveform voltage to the at least one of the two electrodes and a direct-current compensation voltage to the at least one of the two electrodes, to selectively transmit the indicator ions through the analyzer region at a given combination of asymmetric waveform voltage and compensation voltage.

In accordance with yet another aspect of the instant invention there is provided a computer readable storage medium having stored therein data relating to instructions for performing the steps of: receiving a first feedback signal from a FAIMS apparatus, the first feedback signal relating to a compensation voltage value for transmitting a first type of indicator ions through the analyzer region of a FAIMS in the presence of an unknown amount of a vapour of interest and at a given applied asymmetric waveform voltage; receiving calibration data from a memory, the calibration data including a compensation voltage value for transmitting the first type of indicator ions through the analyzer region of a FAIMS in the presence of each one of a plurality of different known amounts of the vapour of interest and at the given applied asymmetric waveform voltage; and, in dependence upon the first feedback signal and the calibration data, determining a value relating to an amount of the unknown amount of the vapour of interest.

BRIEF DESCRIPTION OF THE DRAWINGS

Exemplary embodiments of the invention will now be described in conjunction with the following drawings, in which similar reference numbers designate similar items:

FIG. 6a shows a CV spectrum for the +6 charge state of bovine insulin when a purified carrier gas stream is used;

FIG. 6b shows a CV spectrum for the +6 charge state of bovine insulin when 25 ppm of 2-chlorobutane is added to the carrier gas stream;

FIG. 6c shows a CV spectrum for the +6 charge state of bovine insulin when 50 ppm of 2-chlorobutane is added to the carrier gas stream;

FIG. 6d shows a CV spectrum for the +6 charge state of bovine insulin when 100 ppm of 2-chlorobutane is added to the carrier gas stream;

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
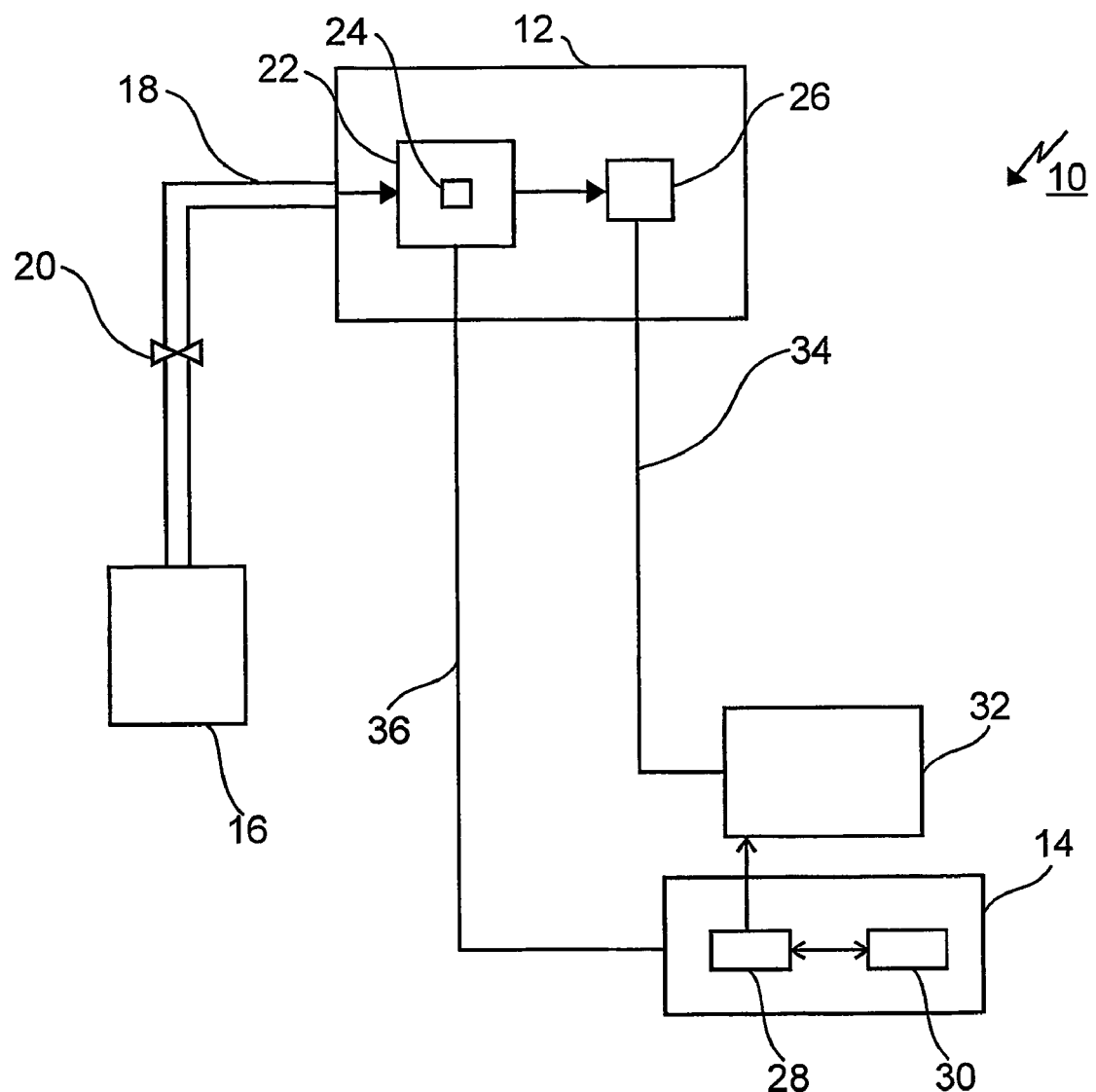
FIG. 1 is a simplified block diagram of an apparatus according to a first embodiment of the instant invention.

Referring to FIG. 1, shown is a simplified block diagram of an apparatus for detecting trace amounts of a vapour in a carrier gas according to a first embodiment of the instant invention. The apparatus, shown generally at 10, includes an analyzer portion 12, a control portion 14 and a gas source portion 16. The gas source portion 16 is in fluid communication with the analyzer portion via a gas transfer line 18. A flow controller or valve 20 is disposed at a point along the length of the gas transfer line 18 for adjusting a flow rate of a gas from the gas source 16. The analyzer portion 12 includes a high field asymmetric waveform ion mobility spectrometer (FAIMS analyzer) 22. For instance, the FAIMS analyer 22 is in the form of one of a cylindrical geometry domed-FAIMS, a side-to-side FAIMS and a parallel plate FAIMS. An ionization source 24 is provided in communication with the FAIMS analyer 22 for providing indicator ions thereto. During use, the indicator ions are transmitted through the FAIMS analyer 22 and detected. For instance, the indicator ions are extracted from the FAIMS analyer 22 for introduction into a mass spectrometer 26. The mass spectrometer 26 provides an electrical signal, which is proportional to a measured ion current of the indicator ions, to the control portion 14 via a first communication line 34. For instance, the control portion 14 is a micro-computer including a processor 28 and a memory 30. The control portion 14 is in electrical communication with a display device 32; for providing information to a user of the apparatus 10. The control portion 14 is also in electrical communication with the FAIMS analer 22 via a second communication line 36 for controlling the application of an asymmetric waveform voltage and a direct current compensation voltage to not illustrated electrodes of the FAIMS analyer 22.

Figure 2:
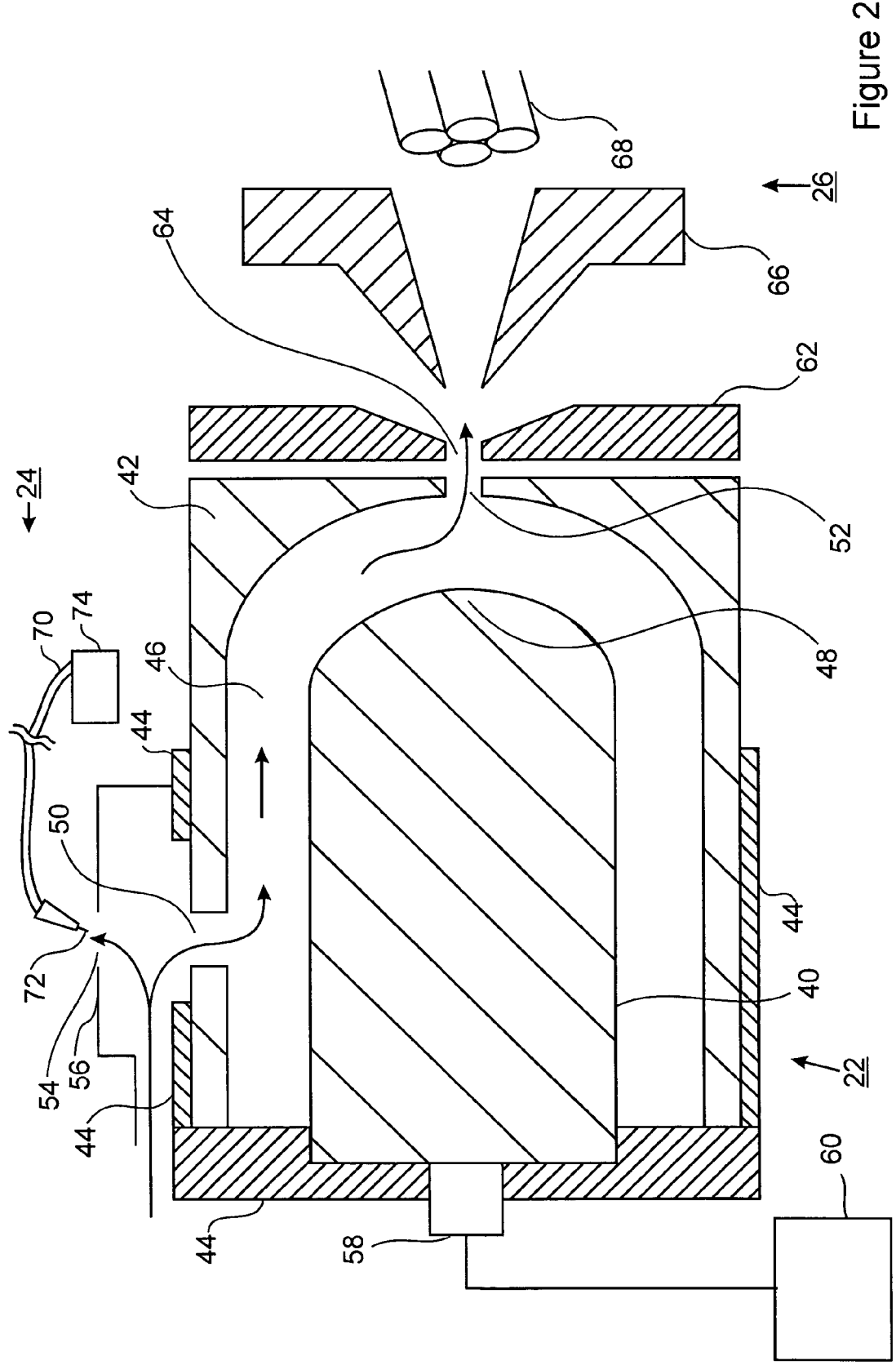
FIG. 2 is a simplified block diagram of a FAIMS analyzer for use with the apparatus according to the first embodiment of the instant invention.

Referring now to FIG. 2, shown is a simplified block diagram of the FAIMS analyzer 22 of the analyzer portion 12 described with reference to FIG. 1. The FAIMS analyzer 22 is in the form of a domed-FAIMS device including inner and outer cylindrical electrodes 40 and 42, respectively. Of course, other electrode geometries are also suitable for use with the instant invention, such as for example one of a parallel plate electrode geometry FAIMS and a side-to-side FAIMS. The inner and outer cylindrical electrodes 40 and 42 are supported by an electrically insulating material 44 in an overlapping, spaced-apart arrangement. The generally annular space between the inner electrode 40 and the outer electrode 42 defines a FAIMS analyzer region 46. The width of the analyzer region is approximately uniform around the circumference of the inner electrode 40, and extends around a curved surface terminus 48 of the inner electrode 40. Inner electrode 40 is provided with an electrical contact 58 through the insulating material 44 for connection to a power supply 60 of the FAIMS analer 22 that during use is capable of applying a high voltage asymmetric waveform voltage (DV) and a low voltage dc compensation voltage (CV) to the inner FAIMS electrode 40. A particular type of ion is transmitted through the analyzer region 46 at a given combination of CV and DV, on the basis of the high field mobility properties of the ion.

An inlet 50 is provided through the outer electrode 42 for introducing indicator ions from the ion source 24 into the analyzer region 46. For example, the ion source 24 is in the form of an electrospray ionization ion source including a liquid delivery capillary 70, a fine-tipped electrospray needle 72 that is held at high voltage (power supply not shown) and a curtain plate 56 serving as a counter-electrode for electrospray needle 72. The liquid delivery capillary 70 is in fluid communication with sample reservoir 74 containing a solution of an indicator ion precursor. Indicator ions are produced by the very strong electric field at the electrospray needle 72 from the solution of an indicator ion precursor. The potential gradient accelerates the indicator ions away from the electrospray needle 72, towards the curtain plate electrode 56. A portion of the indicator ions pass through an orifice 54 in the curtain plate electrode 56, become entrained in a flow of a carrier gas, which is represented in FIG. 2 by a series of closed-headed arrows, and are carried into the FAIMS analyzer region 46. The flow of a carrier gas is provided through the analyzer region 46 to carry the indicator ions toward an outlet 52 located opposite the curved surface terminus 48 of the inner electrode 40. In particular, the flow of a carrier gas is provided from the gas source portion 16 that was described with reference to FIG. 1, and includes a first gas and a trace amount of a vapour of interest. The orifice 54 within the curtain plate electrode 56 allows for the flow of a portion of the carrier gas in a direction that is counter-current to the direction in which the indicator ions are traveling near the ion inlet 50, so as to desolvate the indicator ions before they are introduced into the analyzer region 46. Once inside the FAIMS analyzer region 46, the ions are transmitted through an electric field that is formed within the FAIMS analyzer region 46 by the application of the DV and the CV to the inner FAIMS electrode 40 via the electrical contact 58. Since the electric field also extends around the curved surface terminus 48, the transmitted indicator ions tend to be directed generally radially inwardly towards the outlet 52.

The mass spectrometer 26 is disposed external to the FAIMS analyzer region 46, and includes an orifice plate 62 having an inlet orifice 64 extending therethrough. As will be apparent to one of skill in the art, the size of the inlet orifice 64 is typically very small, being limited by the pumping efficiency of the not illustrated mass spectrometer vacuum system. The inlet orifice 64 in the orifice plate 62 is aligned with the outlet 52 of the domed-FAIMS analyzer 22 such that indicator ions being extracted through the outlet 52 enter the mass spectrometer inlet orifice 64. Those indicator ions that pass through the orifice 64 in the orifice plate 62 travel to a skimmer cone 66 within the differentially pumped region of the mass spectrometer 26, and are analyzed within a mass analyzer 68 on the basis of their mass-to-charge ratio. The mass spectrometer includes a not illustrated detector, such as for instance an electron multiplier, for providing an electrical signal that is proportional to a detected indicator ion current.

Typically, the vapour of interest is a species that is difficult to ionize using conventional atmospheric pressure sources, including: corona discharge; electrospray ionization; radioactive foil; and photoionization, such as for example using UV radiation. It is for this reason that indicator ions are used to determine indirectly the amount of the vapour of interest that is present within the carrier gas. This is a significant departure from all of the prior art relating to FAIMS, in which it is the ions that are produced at the ionization source that are of interest. Preferably, the indicator ions satisfy a number of criteria, as outlined in the following non-exhaustive list. First, it must be possible to form the indicator ions for introduction into the FAIMS analyer 22. Second, the CV spectrum of the indicator ions must be sensitive to the presence of the vapour of interest. For instance, the indicator ions are transmitted through the FAIMS at a different compensation voltage when a trace amount of the vapour of interest is present compared to when the vapour of interest is absent. Third, the magnitude of the CV shift for the indicator ions must change with changing amounts of the vapour of interest. Fourth, the CV shift for the indicator ions should preferably be relatively small with the addition of trace amounts of vapours that are other than of interest; for example, the indicator ions are preferably specific to the vapour of interest. A calibration curve may be prepared for an indicator ion that satisfies the above criteria, relating the CV at which the indicator ion is transmitted to an amount of the vapour of interest within the flow of a carrier gas. Of course, the different points of the calibration curve are obtained at a same DV. Preferably, data relating to the calibration curve is stored in the memory 30 of the control portion 14.

Figure 3:
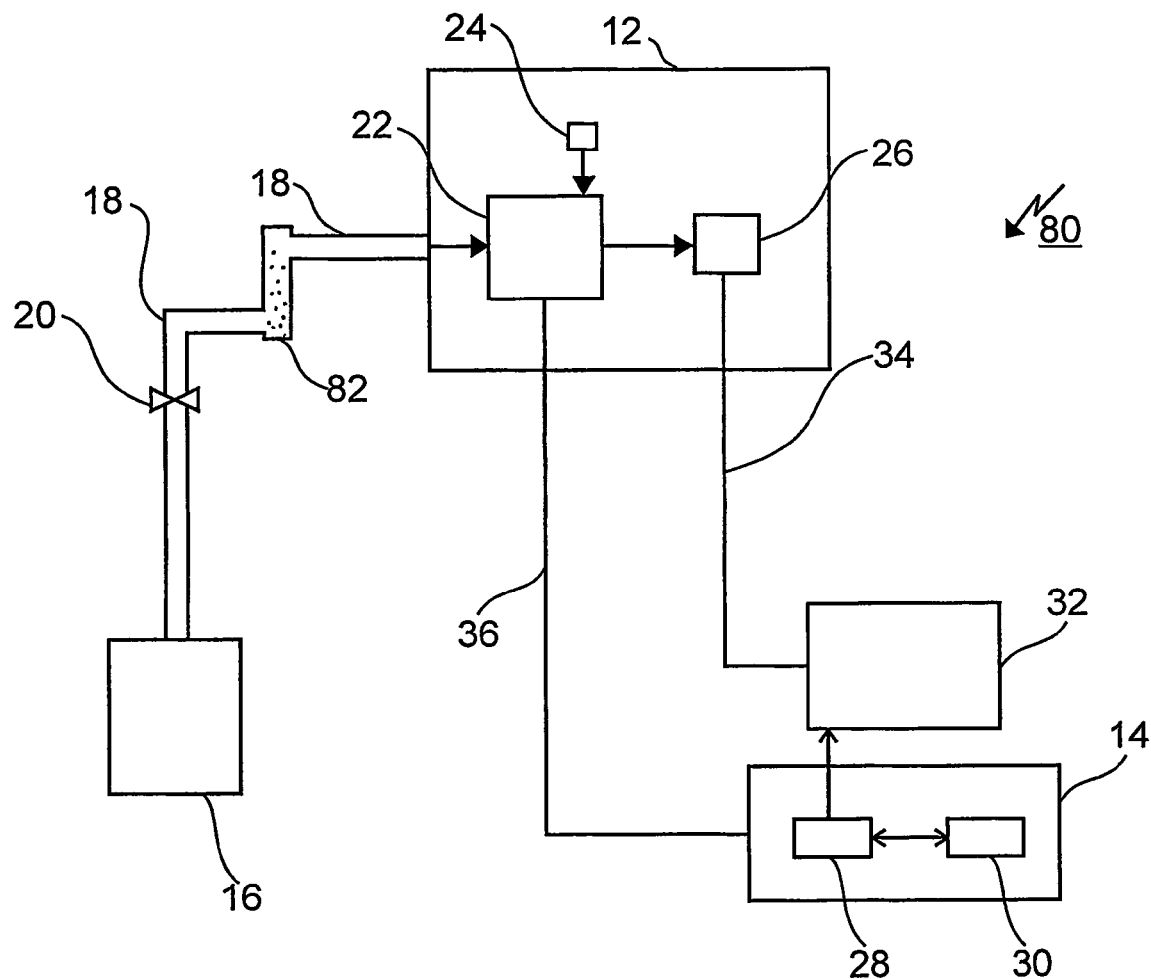
FIG. 3 is a simplified block diagram of another apparatus according to the first embodiment of the instant invention.

Referring now to FIG. 3, shown is a simplified block diagram of another apparatus, shown generally at 80, according to the first embodiment of the instant invention. Elements labeled with the same numerals have the same function as those illustrated in FIG. 1. Apparatus 80 includes a trap 82 that is disposed at a point along the gas transfer line 18 for removing a species contained in the gas flow that is provided from the gas source portion 16. For example, the trap 82 is a molecular sieve filter for removing water vapour from the gas flow. Of course, the trap 82 is by-passed or removed in the event that water vapour is the vapour of interest. In general, the trap contains a material that is selected to remove vapours that are other than of interest, whilst allowing the vapour of interest to pass therethrough. When the vapours that are other than of interest are removed, the observed CV shift for the indicator ions is attributable entirely to the presence of the vapour of interest.

Figure 4:
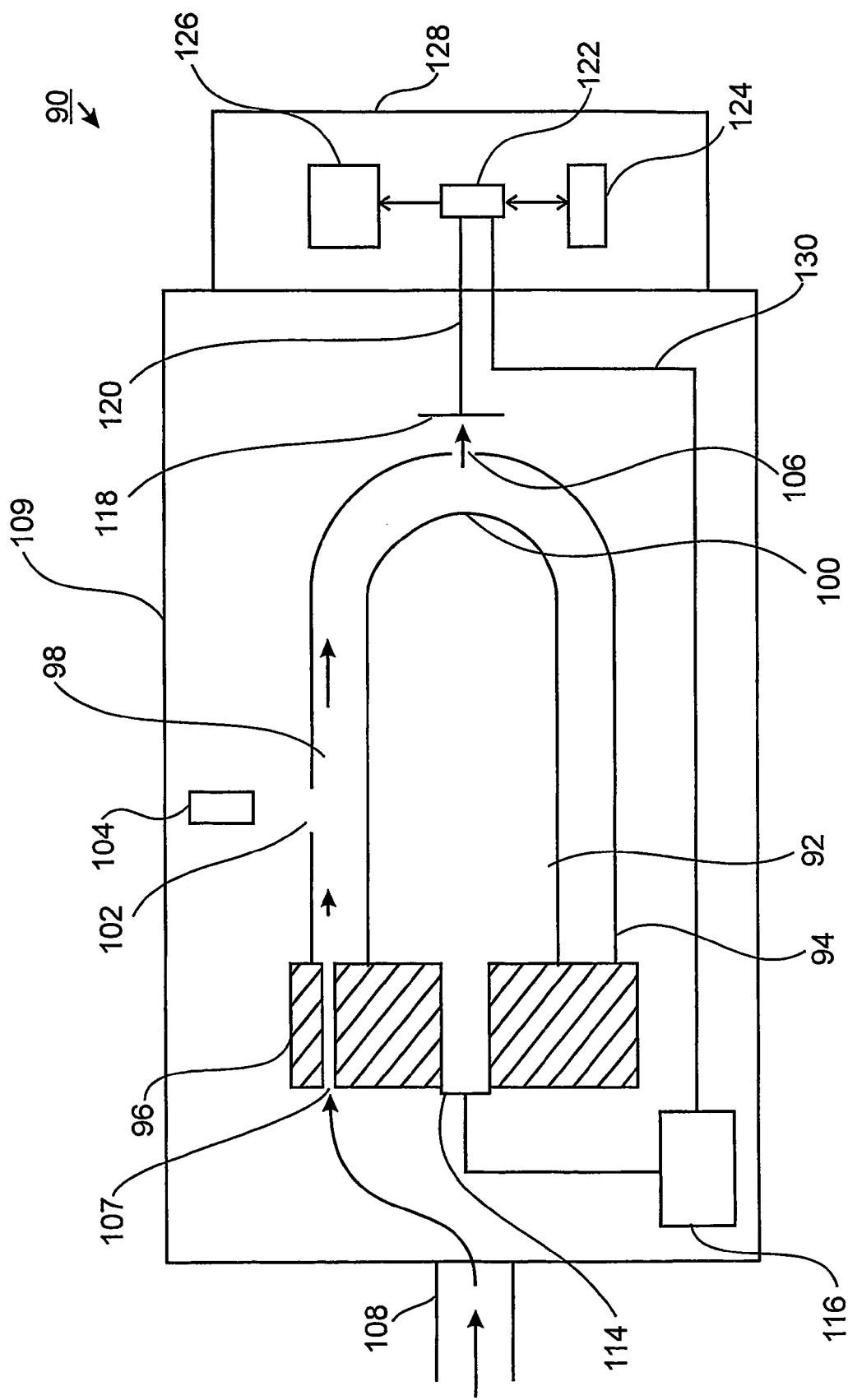
FIG. 4 is a simplified block diagram of an apparatus according to a second embodiment of the instant invention.

Referring now to FIG. 4, shown is a simplified block diagram of an apparatus according to a second embodiment of the instant invention. The apparatus, shown generally at 90, is a portable device including a FAIMS analyzer in the form of a domed-FAIMS. Of course, other electrode geometries are also suitable for use with the instant invention, such as for example one of a parallel plate electrode geometry FAIMS and a side-to-side FAIMS. The domed-FAIMS includes inner and outer cylindrical electrodes 92 and 94, respectively, which are supported by an electrically insulating material 96 in an overlapping, spaced-apart arrangement. The generally annular space between the inner electrode 92 and the outer electrode 94 defines a FAIMS analyzer region 98. The width of the analyzer region is approximately uniform around the circumference of the inner electrode 92, and extends around a curved surface terminus 100 of the inner electrode 92. The inner electrode 92 is provided with an electrical contact 114 through the insulating material 96 for connection to a power supply 116 that during use is capable of applying a high voltage asymmetric waveform voltage (DV) and a low voltage dc compensation voltage (CV) to the inner FAIMS electrode 92. A particular type of ion is transmitted through the analyzer region 98 at a given combination of CV and DV, on the basis of the high field mobility properties of the ion.

An inlet 102 is provided through the outer electrode 94 for introducing indicator ions from an ion source 104 into the analyzer region 98. The indicator ions pass through the inlet 102, where they become entrained in a flow of a carrier gas, which is represented in FIG. 4 by a series of closed-headed arrows. The flow of a carrier gas is provided through the analyzer region 98 to carry the indicator ions toward an outlet 106 located opposite the curved surface terminus 100 of the inner electrode 92.

Referring still to FIG. 4, the flow of a carrier gas is provided from a gas-sampling portion 108, for instance a probe flexibly mounted to a housing 109 to obtain samples of an atmosphere external to the housing 109 for detection and analysis. The sampling portion includes not illustrated tubing for providing the flow of a carrier gas from the sampling portion 108, through an opening 107 in the insulator material 96, and into the FAIMS analyzer region 98. Preferably, at least one pump is provided to draw the sampled atmosphere through the analyzer region 98. While not shown, the pump may be a vortex, diaphragm, vacuum or like pump capable of providing a slight negative pressure within the FAIMS analyzer region 98. In a portable mode, rechargeable batteries, not shown, power the pump.

A detector, for instance an electrometric detector 118, is disposed external to the FAIMS analyzer region 98. Those indicator ions that pass through the analyzer region 98 and out of the outlet 106 impinge upon the electrometric detector 118 and are detected. The electrometric detector 118 provides an electrical signal that is proportional to a detected indicator ion current via a first communication line 120, to a processor 122 in communication with a memory 124 and a display device 126. The processor 122, memory 124 and display device are preferably contained within a separate housing 128. The processor 122 is also in electrical communication with the power supply 116 of the FAIMS analyzer via a second communication line 130 for controlling the application of an asymmetric waveform voltage and a direct current compensation voltage to the inner electrode 92.

The apparatus 90 includes a single ionization source 104 for providing indicator ions within the analyzer region 98. The ionization source 104 includes a source of indicator ion precursors, which are ionized to produce the indicator ions. Optionally, the ionization source 104 includes a source of a first indicator ion precursor and a source of a second indicator ion precursor. Accordingly, the ionization source 104 is for forming first and second indicator ions for introduction into the analyzer region 98. Optionally, the user selects one of the first and second precursor ions in dependence upon the vapour of interest. Further optionally, the processor 122 performs multiple analysis of a same vapour of interest using each one of the first and second indicator ions either in parallel or in series. In any of the optional embodiments, the sources of indicator ion precursors may be provided as a user replaceable unit or as a permanent unit. Of course, user replaceable units allow the user to switch between different indicator ions so as to support the analysis of a wider variety of different vapours of interest.

When the atmosphere external to housing 109 is substantially air, the vapour of interest is considered to be a user-defined species that is present within the air. For instance, the user-defined species is an environmental contaminant not normally found in air or undesirable when found in air.

The ion source 104 may include any suitable ionizer, such as for example one of a beta-source ionizer, a corona discharge ionizer, an electrospray ionizer and a photoionization source. While beta-ionization sources require regulatory agency licensing, they avoid additional electrical power requirements which is important for portable instruments. If electrical power is not a concern, it is preferable to utilize electronic or photoionization when portability is desired. Of course, when the ion source 104 is provided in the form of an electrospray ionizer, a separate desolvation region associated with the ion source is required for desolvating the ions prior to introduction into the analyzer region 98. A suitable desolvation region, in the form of a curtain plate assembly, was described with reference to FIG. 2.

Figure 5:
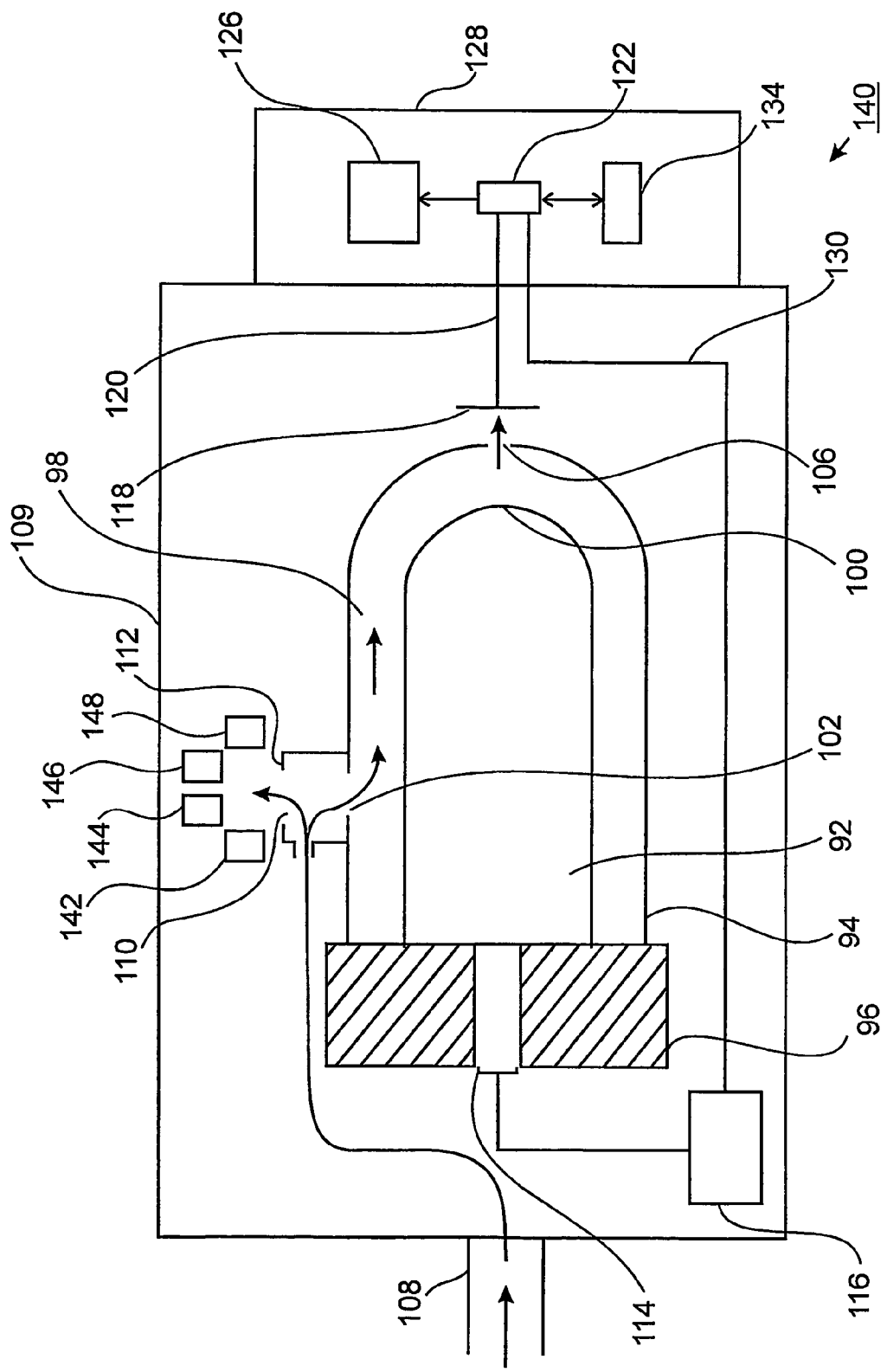
FIG. 5 is a simplified block diagram of another apparatus according to the second embodiment of the instant invention.

Referring now to FIG. 5, shown is a simplified block diagram of another apparatus according to the second embodiment of the instant invention. Elements labeled with the same numerals have the same function as those illustrated in FIG. 4. The apparatus shown generally at 140 includes four ionization sources 142, 144, 146 and 148. Each ionization source 142, 144, 146 and 148 includes a source of indicator ion precursors, which are ionized to produce the indicator ions. Preferably, each ionization source 142, 144, 146 and 148 is for providing a different type of indicator ion within the FAIMS analyzer region 98. This allows the apparatus 140 to be used to detect four or more different vapours of interest. Alternatively, each of the four ionization sources is used, either in series or in parallel, so as to perform multiple analysis of a same vapour of interest, and thereby improve the reliability of the results. Optionally, each source of indicator ion precursors may be provided as a user replaceable unit or as a permanent unit. Of course, user replaceable units allow the user to switch between different indicator ions so as to support the analysis of a wider variety of different vapours of interest.

Each ionization source 142, 144, 146 and 148 includes any suitable ionizer, such as for example one of a beta-source ionizer, a corona discharge ionizer, an electrospray ionizer and a photoionization source. While beta-ionization sources require regulatory agency licensing, they avoid additional electrical power requirements, which is important for portable instruments. If electrical power is not a concern, it is preferable to utilize electronic or photoionization when portability is desired. Of course, at least some of the ionization sources 142, 144, 146 and 148 may be different types of ionization sources, to allow a user to select a most appropriate type of ionization source for producing a given indicator ion. FIG. 5 includes a curtain plate electrode 112 having an orifice 110. The flow of a carrier gas that is introduced into the curtain plate assembly splits into two, with a first portion of the flow passing outward through the orifice 110 in a direction that is counter current to the arriving indicator ions, so as to facilitate desolvation of indicator ions that are produced using certain ionization techniques. A second portion of the flow of a carrier gas carries the indicator ions inwardly through the inlet 102, and through the analyzer region 98 toward the outlet 106. The curtain plate assembly is desired when at least one of the ionization sources 142, 144, 146 and 148 is an electrospray ionization source.

Particular features of the invention will now be illustrated using two specific and non-limiting examples in which the +6 charge state of bovine insulin and the +7 charge state of bovine insulin are used as indicator ions for detecting trace amounts of 2-chlorobutane in a carrier gas stream.

EXAMPLE 1

The +6 charge state of bovine insulin was used as an indicator ion for detecting trace amounts of 2-chlorobutane in a carrier gas stream. Two separate gas sources, one containing industrial nitrogen gas and the other containing 1000 ppm 2-chlorobutane in nitrogen gas, were used. Gas from each one of the two separate gas sources were mixed using a tee assembly and introduced as the flow of a carrier gas into a FAIMS device. Trace levels of 2-chlorobutane in the carrier gas of 25 ppm, 50 ppm, 75 ppm, and 100 ppm. were obtained by setting the flow rate of the gas mixture containing 1000 ppm 2-chlorobutane in nitrogen to 0.03 L/min, 0.06 L/min, 0.09 L/min, and 0.12 L/min, respectively. In each case, the flow rate of the industrial nitrogen gas was adjusted to keep the total flow at 1.2 L/min.

FIGS. 6*a*–6*d* show four CV spectra that were acquired for the +6 charge state of bovine insulin using a carrier gas containing 0, 25, 50 and 100 ppm of 2-chlorobutane, respectively. The four spectra were obtained using identical operating conditions except for the addition of 0, 25, 50, and 100 ppm of 2-chlorobutane to the carrier gas stream. With the experimental set-up used in collecting this data, the minimum amount of 2-chlorobutane vapour that was added to the stream of purified gas was 25 ppm. The purified gas lacks the vapour of interest, or similarly active compounds, which affect the CV of the indicator ions. A comparison of the CV spectrum shown at FIG. 6*a* and the CV spectrum shown at FIG. 6*b* reveals a significant change in the CV of transmission, that is from CV approximately −12.3 to CV approximately −10.8 V. Such a significant change in the CV of transmission indicates that the detection limit using this method is likely lower than 25 ppm for 2-cholorbutane. In this example, another separation parameter was observed. In addition to the shift in CV, a small change in the separation capabilities is also observed at this low level of 2-chlorobutane, as evidenced by the appearance of shoulder on the more negative side of the main peak in FIG. 6b.

With reference to FIGS. 6c and 6d, increasingly large CV shifts for the main peak and increasingly improved separation capabilities are observed as the level of 2-chlorobutane is increased to 50 ppm and 100 ppm.

EXAMPLE 2

Figure 7A:
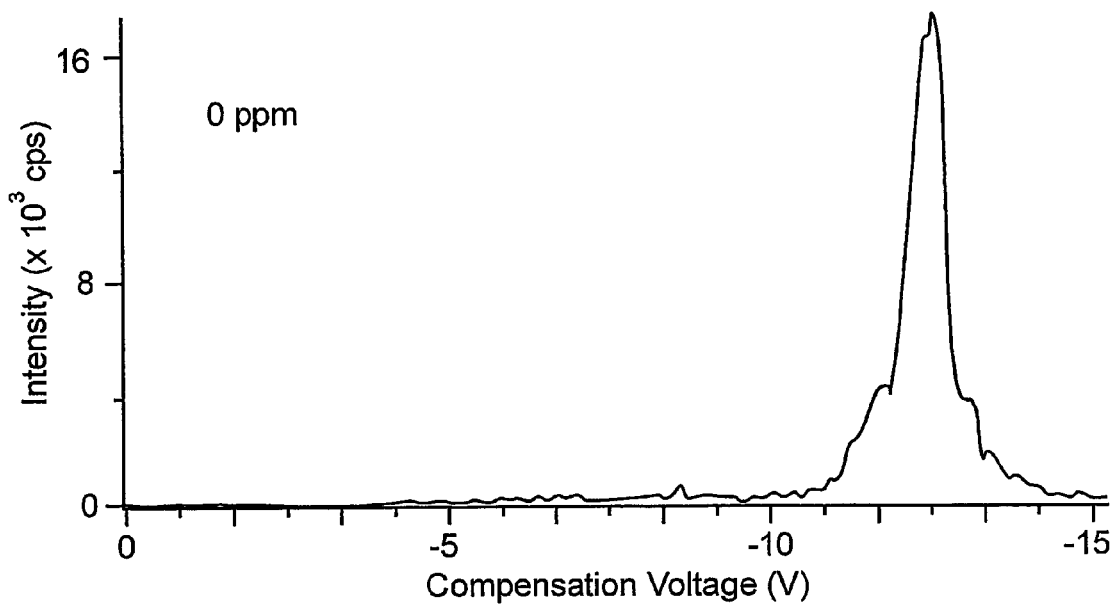
FIG. 7a shows a CV spectrum for the +7 charge state of bovine insulin when a purified carrier gas stream is used.
Figure 7B:
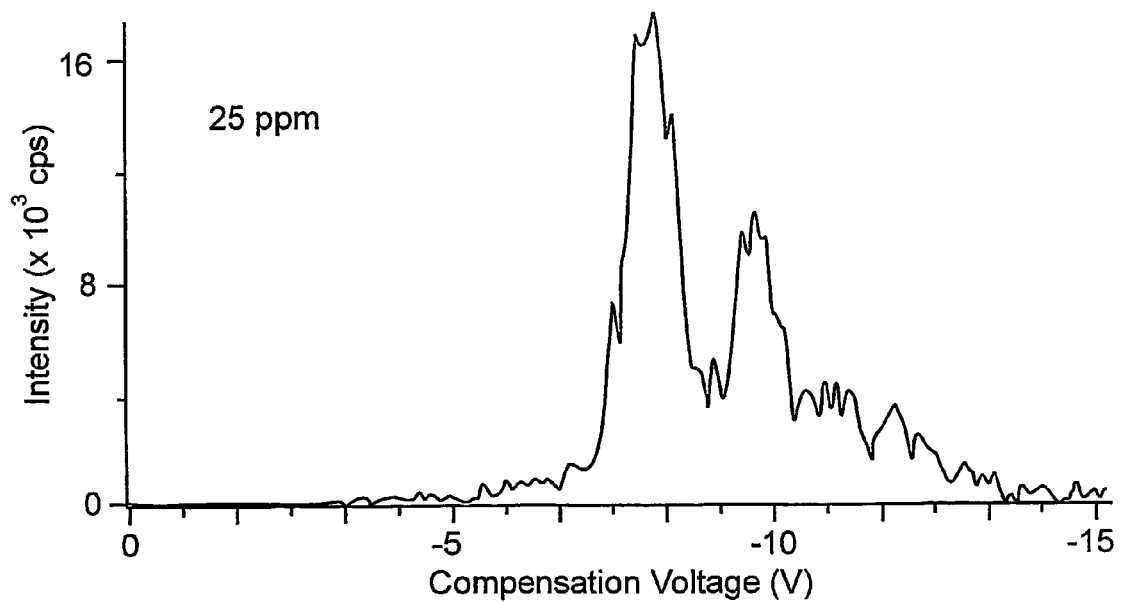
FIG. 7b shows a CV spectrum for the +7 charge state of bovine insulin when 25 ppm of 2-chlorobutane is added to the carrier gas stream.

For comparison, the +7 charge state of bovine insulin was also used as an indicator ion for detecting trace amounts of 2-chlorobutane in a carrier gas stream. FIG. 7a shows a CV spectrum for the bovine insulin ion at the +7 charge state with no 2-chlorobutane present, and FIG. 7b shows a CV spectrum for the bovine insulin ion at the +7 charge state with 25 ppm 2-chlorobutane present. Although, the signal intensity for this charge state is significantly lower than for the +6 charge state, there is an unexpected, and a dramatic change in the CV spectrum when only 25 ppm of 2-chlorobutane is used. For the same amount of 2-chlorobutane in the carrier gas, the separation capabilities have improved dramatically for the +7 charge state. Furthermore, the detection limit for 2-chlorobutane in the gas phase that could be obtained by monitoring changes in the CV spectrum of the +7 charge state is anticipated to be significantly lower than it is for the +6 charge state. Based on FIG. 7b, the detection limit for 2-chlorobutane in the gas phase using changes in the CV spectrum of the +7 charge state should likely be significantly lower than 25 ppm.

The use of FAIMS for the detection of non-ionized components in a stream of a carrier gas differs substantially from existing technology. In this approach the lower limit of detection of the component in a stream is not limited by the disappearance of the signal registered by, for example, a mass spectrometer. Although the signal intensity shown in FIG. 7b is low, a higher signal for this ion may be detected using a higher concentration of bovine insulin. Since it is not the signal intensity of the bovine insulin ion that is measured to detect 2-chlorobutane, but rather the shifts in the peaks of bovine insulin, the limit of detection of 2-chlorobutane is quite independent from the signal intensity registered by the mass spectrometer.

Figure 8:
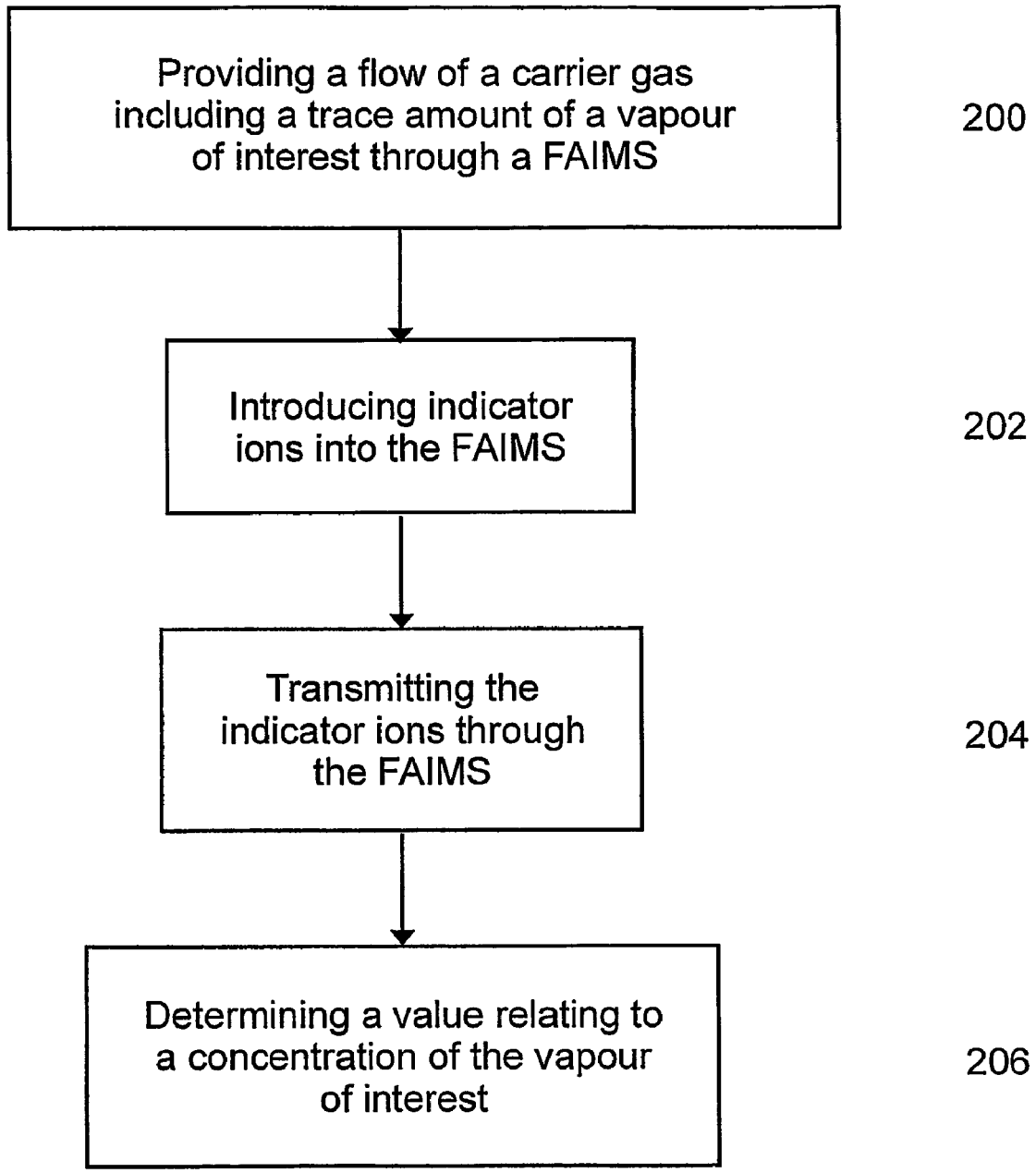
FIG. 8 is a simplified flow diagram for a method of detecting trace amounts of a vapour of interest in a carrier gas.

Referring now to FIG. 8, shown is a simplified flow diagram for a method of detecting trace amounts of a vapour in a carrier gas. At step 200, a flow of a carrier gas including a trace amount of a vapour of interest is provided through an analyzer region of a FAIMS. As described supra the carrier gas including a trace amount of a vapour of interest is provided from, for example, one of a sample container and an atmosphere that is external to a housing of the FAIMS. The carrier gas is optionally one of a single gas and a mixture of gases, such as for instance one of a mixture of two purified gases and air. In either case, the carrier gas includes a trace amount of a vapour of interest that is to be analyzed indirectly. To this end, indicator ions are introduced into the FAIMS at step 202. In particular, the indicator ions are selected on the basis of their sensitivity to changes in their CV spectrum in the presence of different amounts of the vapour of interest. At step 204, the indicator ions are transmitted through the FAIMS analyzer, in the presence of the vapour of interest, at a particular combination of applied CV and DV. At step 206, a value relating to a concentration of the vapour of interest is determined based upon a comparison of the CV that is applied at step 204 to calibration data relating to compensation voltage values for transmitting the indicator ions at a same DV for each of a plurality of different known amounts of the vapour of interest.

Figure 9:
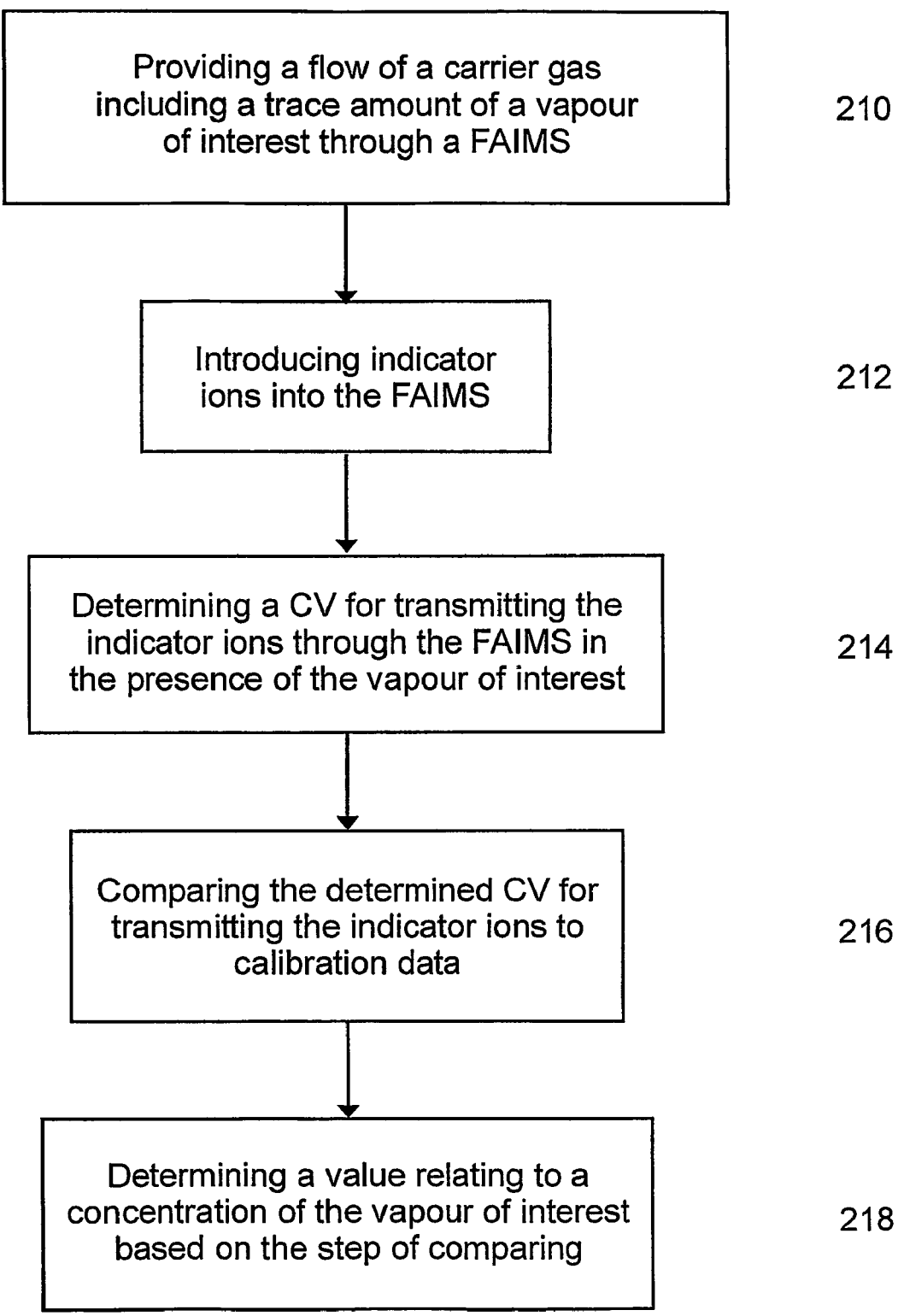
FIG. 9 is a simplified flow diagram for another method of detecting trace amounts of a vapour of interest in a carrier gas.

Referring now to FIG. 9, shown is a simplified flow diagram for another method of detecting trace amounts of a vapour of interest in a carrier gas. At step 210, a flow of a carrier gas including a trace amount of a vapour of interest is provided through an analyzer region of a FAIMS. As described supra the carrier gas including a trace amount of a vapour of interest is provided from, for example, one of a sample container and an atmosphere that is external to a housing of the FAIMS. The carrier gas is optionally one of a single gas and a mixture of gases, such as for instance one of a mixture of two purified gases and air. In either case, the carrier gas includes a trace amount of a vapour of interest that is to be analyzed indirectly. To this end, indicator ions are introduced into the FAIMS at step 212. For example, the indicator ions are selected on the basis of their tendency to be transmitted through the FAIMS at different CV values in the presence of different amounts of the vapour of interest. At step 214, the indicator ions are transmitted through the FAIMS analyzer, in the presence of the vapour of interest, and a CV spectrum corresponding to the indicator ions is obtained by varying the applied CV whilst applying a constant asymmetric waveform voltage. The CV is varied over a range of values including a CV value that is expected absent the vapour of interest in the carrier gas and CV values observed in the presence of known concentrations of the vapour of interest. From the CV spectrum, an optimum CV value for transmitting the indicator ions through the FAIMS is determined. At step 216, the determined CV for transmitting the indicator ions is compared to calibration data obtained under similar operating conditions using different known amounts of the vapour of interest. A value relating to a concentration of the vapour of interest is determined at step 218 on the basis of the step of comparing performed at step 216.

A disadvantage of the methods described with reference to FIGS. 8 and 9 is the specificity in that the compound that is detected cannot be identified unambiguously. Clearly some other compound, other than 2-chlorobutane, could be added to the carrier gas and might cause a shift in the CV spectrum, of the type observed in FIGS. 6 and 7. The reliable detection of compounds by this indirect analytical approach requires specificity through selection of the indicator ion, a comparative analysis of results from a combination of selected indicator ions, or the investigation of the different CV spectra of one or more indicator ions at different DV values. For example, when the results from a series of indicator ions are taken together, there is a greater likelihood that the results are a consequence of the vapour of interest. This series of indicator ions could be produced simultaneously by an ionization method such as electrospray ionization. Since the vapour of interest itself is not being ionized, the selection of an appropriate method of ionization is dependent on the selection of the indicator ion or ions. In the above-cited examples, electrospray ionization is ideal for producing an indicator ion for the target analyte 2-chlorobutane. Other indicator ions could be generated by corona discharge, laser desorption ionization, chemical ionization, radioactive sources, ultraviolet radiation etc., as appropriate for the formation of the indicator ion. Since the vapour of interest is not ionized, the analytical system is not required to form, separate or detect this vapour in its ionic form. The vapour of interest remains substantially unchanged.

Figure 10:
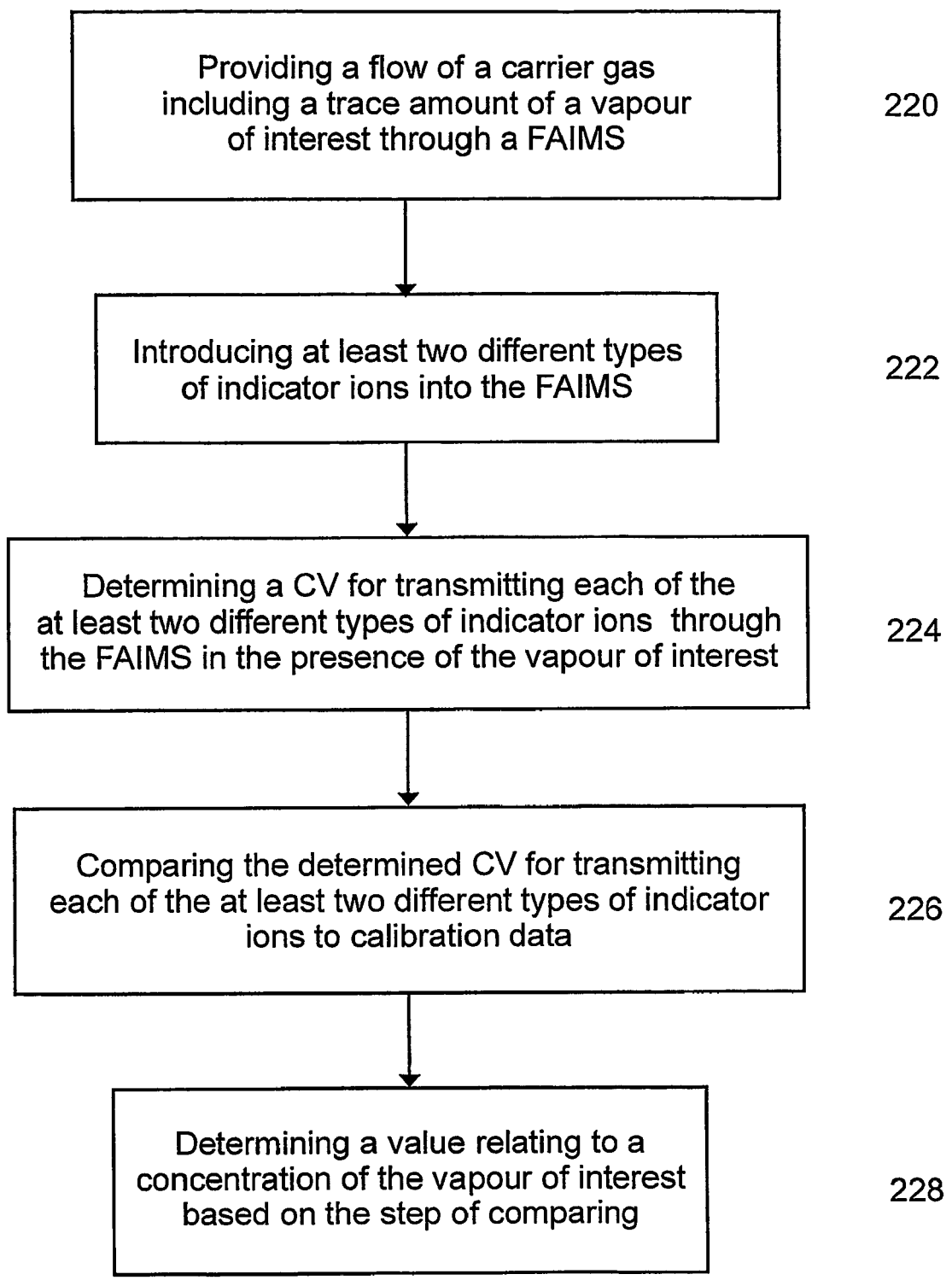
FIG. 10 is a simplified flow diagram for yet another method of detecting trace amounts of a vapour of interest in a carrier gas.

Referring now to FIG. 10, shown is a simplified flow diagram of yet another method of detecting trace amounts of a vapour of interest in a carrier gas. At step 220, a flow of a carrier gas including a trace amount of a vapour of interest is provided through an analyzer region of a FAIMS. As described supra the carrier gas including a trace amount of a vapour of interest is provided from, for example, one of a sample container and an atmosphere that is external to a housing of the FAIMS. The carrier gas is optionally one of a single gas and a mixture of gases, such as for instance one of a mixture of two purified gases and air. In either case, the carrier gas includes a trace amount of a vapour of interest that is to be analyzed indirectly. To this end, indicator ions are introduced into the FAIMS at step 222. In particular, at least two different types of indicator ions are introduced into the FAIMS. Each of the two types of indicator ions is selected on the basis of their tendency to be transmitted through the FAIMS at different CV values in the presence of different amounts of the vapour of interest. Preferably, the CV spectra of the at least two different types of indicator ions are affected by the presence of trace amounts of the vapour of interest, and not by trace amounts of vapours that are other than of interest. As discussed above, when the results from a series of different indicator ions are taken together, there is a greater likelihood that the results are a consequence of the vapour of interest. At step 224, the indicator ions are transmitted through the FAIMS analyzer, in the presence of the vapour of interest, and a CV spectrum corresponding to each one of the at least two types of indicator ions is obtained by varying the applied CV whilst applying a constant asymmetric waveform voltage. Optionally, the CV spectra for the at least two types of indicator ions are obtained in series or in parallel. For each type of indicator ion, the CV is varied over a range of values including a CV value that is expected absent the vapour of interest in the carrier gas, and CV values expected at known concentrations of the vapour of interest. From the CV spectrum for each one of the at least two types of indicator ions, an optimum CV value for transmitting each different type of indicator ion through the FAIMS is determined. At step 226, the determined CV for transmitting each different type of indicator ions is compared to calibration data obtained under similar operating conditions using different known amounts of the vapour of interest. A value relating to a concentration of the vapour of interest is determined at step 228 on the basis of the step of comparing performed at step 226.

The ability to detect the presence of compounds indirectly using the methods and apparatus described herein is of particular importance for the analysis of trace compounds that cannot be easily ionized, such as for example for example polyaromatics and other hydrocarbons.

Figure 11:
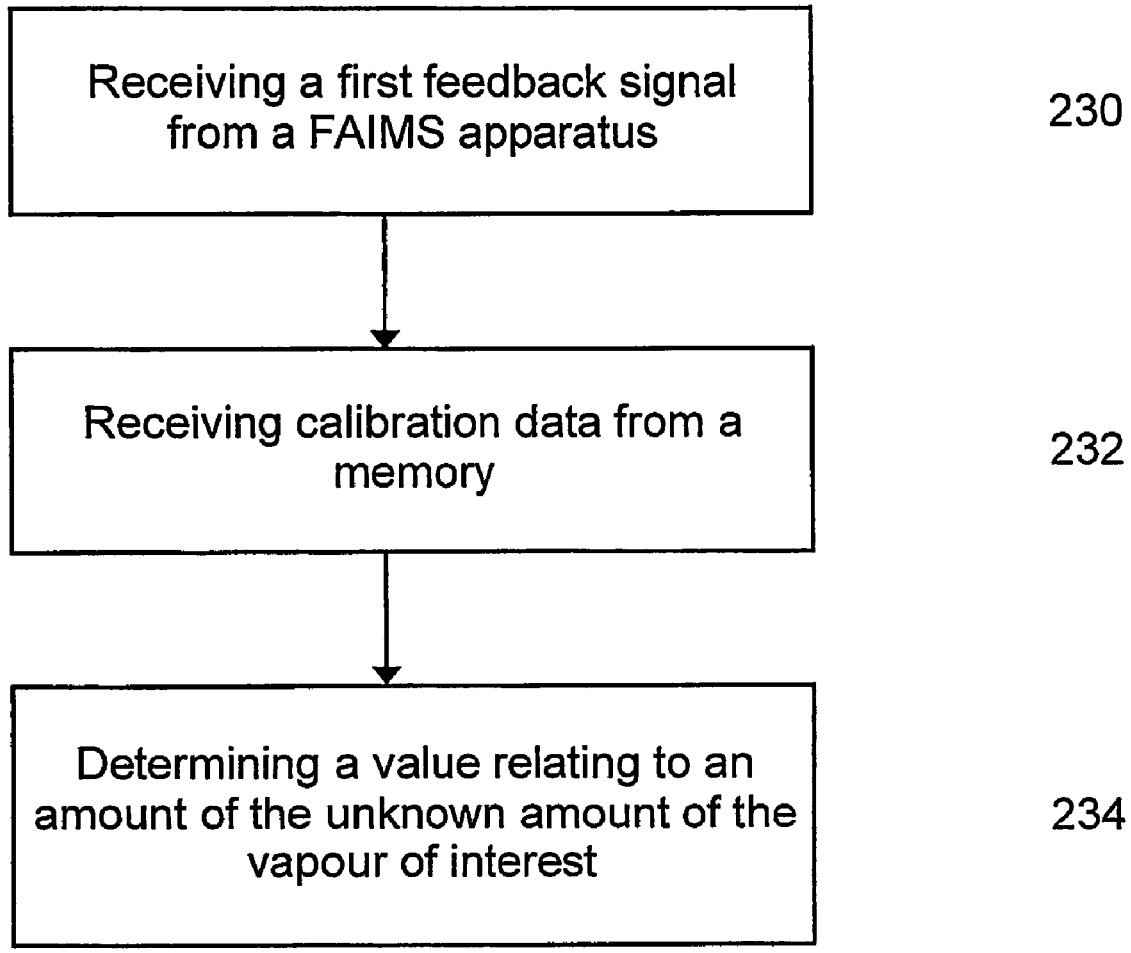
FIG. 11 is a simplified flow diagram showing process steps carried out by a processor in response to data stored therein and relating to instructions for determining a value relating to an unknown amount of a vapour of interest.

Preferably, the value relating to a concentration of the vapour of interest is determined automatically. For instance, the processor 28 that was described with reference to FIGS. 1 and 3 or the processor 122 that was described with reference to FIGS. 4 and 5, has stored therein data relating to instructions for performing the steps that are involved in determining automatically the value relating to a concentration of the vapour of interest. Referring now to FIG. 11, shown is a simplified flow diagram of the steps that are performed by the processor 28 or the processor 122 in order to determine automatically the value relating to a concentration of the vapour of interest. At step 230, the processor receives a first feedback signal from a FAIMS apparatus. The first feedback signal preferably includes data relating to at least one of a compensation voltage value for transmitting a first type of indicator ions through the analyzer region of a FAIMS in the presence of an unknown amount of a vapour of interest and at a given applied asymmetric waveform voltage. More preferably, the first feedback signal also includes information relating to a detected ion intensity at the compensation voltage value. At step 232, the processor receives calibration data from a memory, the calibration data including a compensation voltage value for transmitting the first type of indicator ions through the analyzer region of a FAIMS in the presence of each one of a plurality of different known amounts of the vapour of interest and at the given applied asymmetric waveform voltage. In dependence upon the first feedback signal and the calibration data, the processor determines at step 234 a value relating to an amount of the unknown amount of the vapour of interest.

Optionally, the above-mentioned steps are performed automatically using a second type of indicator ions. To this end, the processor may also have stored therein data relating to instructions for repeating the above-mentioned steps using the second type of indicator ions. Furthermore, the processor may also have stored therein data relating to instructions for comparing the value relating to an amount of the unknown amount of the vapour of interest determined using the first type of indicator ion and a value relating to an amount of the unknown amount of the vapour of interest determined using the second type of indicator ion. Preferably, the processor also has stored therein data relating to instructions for providing a trusted value relating to an amount of the unknown amount of the vapour of interest based upon a result of the two comparisons. The trusted value is obtained when, for example, a plurality of different types of indicator ions provide similar values for the unknown amount of the vapour of interest.

Figure 12:
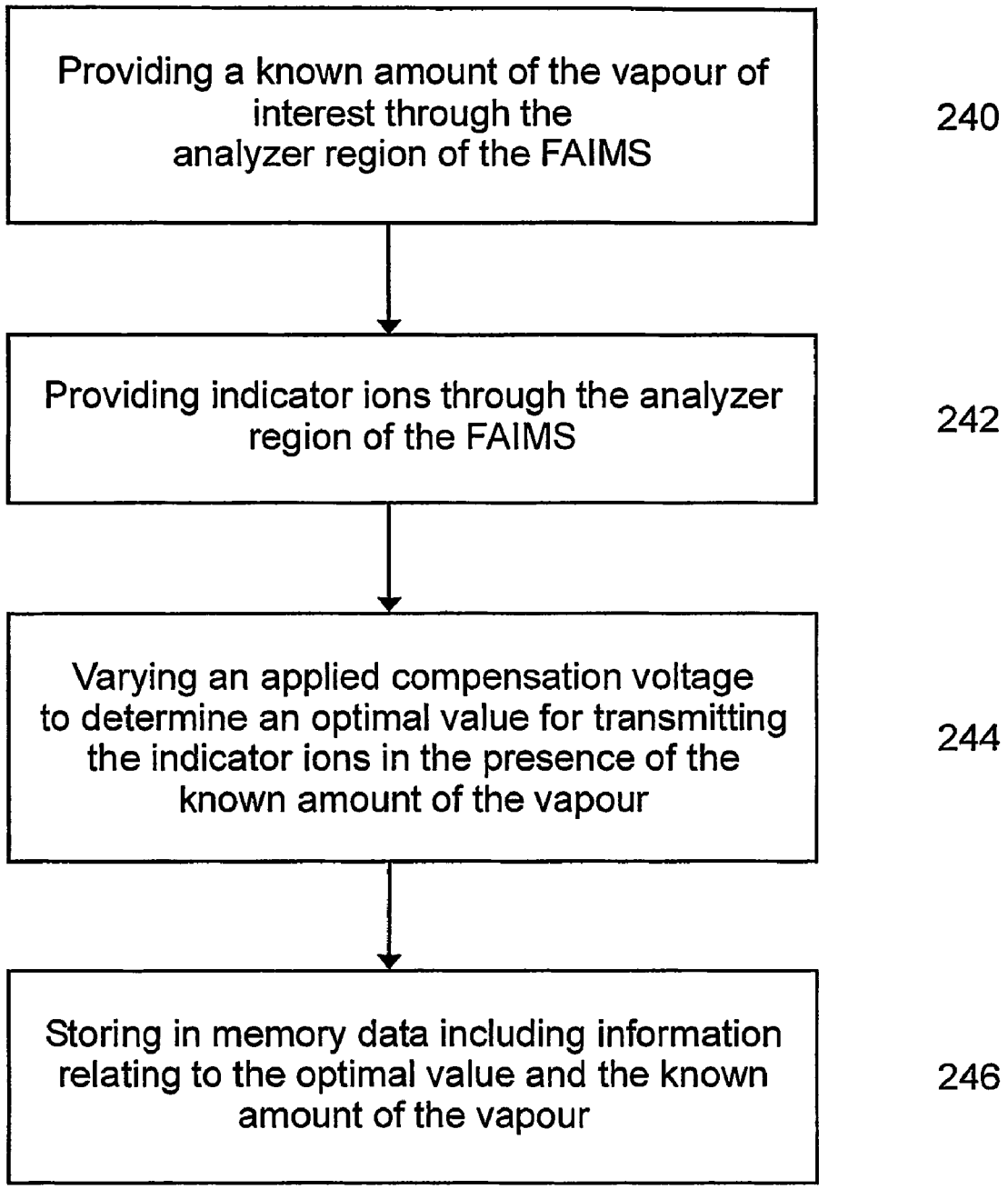
FIG. 12 is a simplified flow diagram showing process steps carried out by a processor in response to data stored therein and relating to instructions for obtaining automatically calibration data for a type of indicator ions.

Optionally, the processor has stored therein data relating to instructions for performing the steps that are involved in obtaining and storing calibration data relating to CV values for transmitting a type of indicator ions through a FAIMS in the presence of a plurality of different known amounts of a vapour of interest. Of course, the processor must be in communication with a delivery system for introducing a carrier gas stream containing the plurality of different known amounts of the vapour of interest. Referring now to FIG. 12, shown is a simplified flow diagram of the steps that are performed by the processor 28 or the processor 122 in order to obtain automatically calibration data. At step 240, the processor introduces a known amount of the vapour of interest mixed with a carrier gas into the analyzer region of the FAIMS, at a given applied asymmetric waveform voltage. At step 242, the processor provides a type of indicator ions through the analyzer region of the FAIMS, in the presence of the known amount of the vapour of interest. At step 244, the processor provides a signal to an electrical controller of the FAIMS, for varying the compensation voltage applied to the FAIMS, so as to determine an optimal compensation voltage for transmitting the type of indicator ions in the presence of the known amount of the vapour of interest and at the given applied asymmetric waveform voltage. At step 246, the processor stores data in a memory, the data including information relating to the determined optimal compensation voltage for transmitting the type of indicator ions in the presence of the known amount of the vapour of interest and at the given applied asymmetric waveform voltage. Preferably, the above-mentioned steps are repeated using a plurality of different known amounts of the vapour of interest. Optionally, calibration data is obtained automatically for a plurality of different indicator ions.

Figure 13A:
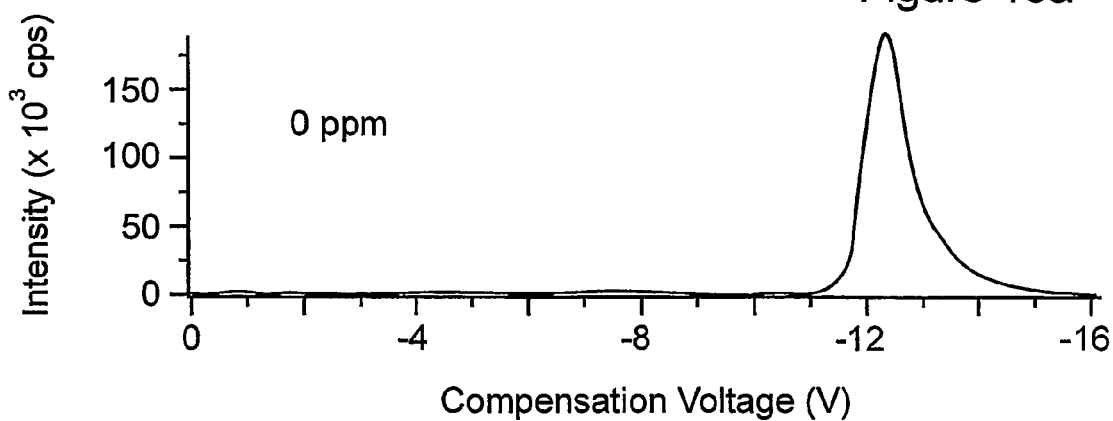
FIG. 13a shows a CV spectrum for an indicator ion when a purified carrier gas stream absent a hazardous vapour is provided within a FAIMS.
Figure 13B:
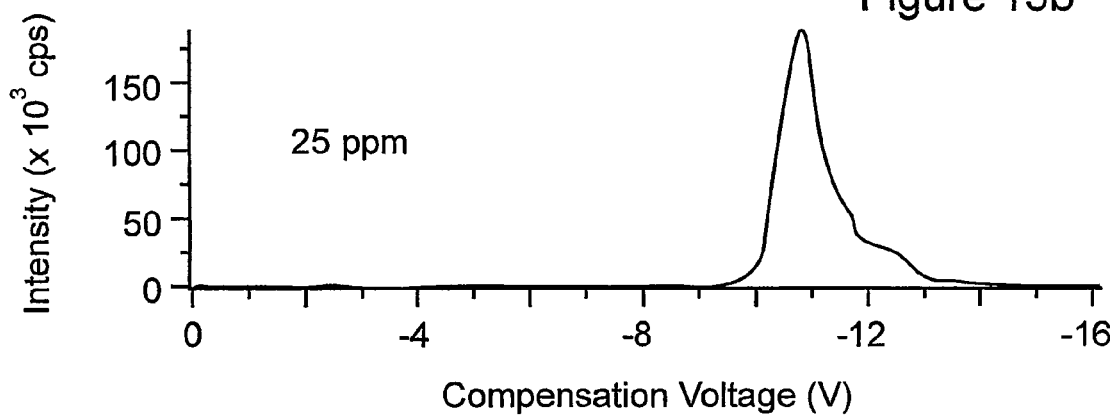
FIG. 13b shows a CV spectrum for an indicator ion when 25 ppm of the hazardous vapour is provided within the FAIMS; and, FIG. 13c shows a CV spectrum for an indicator ion when 50 ppm of the hazardous vapour is provided within the FAIMS.
Figure 13C:
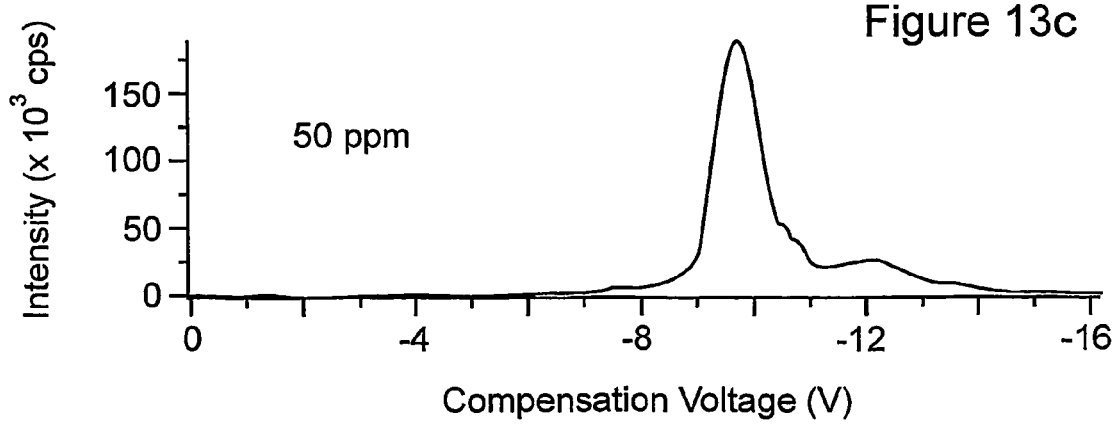

Of course, it is not a crucial feature of the instant invention that a value relating to a concentration of the vapour of interest is determined. For instance, a particular vapour of interest may have a certain threshold concentration above which the vapour becomes hazardous. Accordingly, for some applications is it necessary only to obtain an indication as to whether or not the vapour is present at a concentration that exceeds the certain threshold concentration. To illustrate this concept, reference is made to FIGS. 13a to 13c, which show a series of hypothetical CV spectra obtained for a hypothetical indicator ion in the presence of 0 ppm, 25 ppm and 50 ppm of a hypothetical hazardous vapour. If, for example, the hypothetical hazardous vapour has a threshold concentration of approximately 50 ppm, then a method could be envisaged in which the compensation voltage applied to the FAIMS is scanned over a narrow range between −9 V and −12 V. If a peak maximum is not detected during a scan, then an alarm or a signal is activated to indicate that the hypothetical vapour has reached the threshold concentration, for example, the peak maximum has been shifted to a CV value more positive than −9 V as a result of the unacceptably high concentration of the hazardous vapour. Of course, if peak maximum is detected during the scan, as would be the case when 0 ppm or 25 ppm of the hypothetical vapour is present, then no alarm or signal is activated. This method of signaling a dangerous or hazardous level of a vapour in a sampled carrier gas stream is particularly well suited for detecting poisonous, explosive, carcinogenic, etc. vapours at levels which pose a particular hazard. This method is particularly well suited for use with field portable devices, in particular hand-held FAIMS devices.

Numerous other embodiments may be envisaged without departing from the spirit and scope of the invention.

What is claimed is:

1. A method of detecting trace levels of a vapour in a carrier gas, comprising the steps of:
    a) providing a flow of a carrier gas through an analyzer region of a high field asymmetric waveform ion mobility spectrometer, the carrier gas including a first gas and a trace amount of a vapour;
    b) introducing a first type of indicator ions into the analyzer region;
    c) determining a compensation voltage for transmitting the first type of indicator ions through the analyzer region in the presence of the flow of a carrier gas and at a given asymmetric waveform voltage; and,
    d) comparing the determined compensation voltage to calibration data relating to a compensation voltage for transmitting the first type of indicator ions through the analyzer region at the given asymmetric waveform voltage in the presence of each of a plurality of different known trace amounts of the vapour mixed with the first gas.

2. A method according to claim 1, wherein the trace amount of a vapour in the carrier gas is a trace amount of a vapour other than water.

3. A method according to claim 1, comprising a step of determining an amount of the vapour that is present in the carrier gas based upon a result of the step of comparing.

4. A method according to claim 1, absent a step of ionizing a substantial portion of the vapour.

5. A method according to claim 1, comprising a step of determining a compensation voltage for transmitting the first type of indicator ions through the analyzer region in the presence of the flow of a carrier gas and at a second different asymmetric waveform voltage.

6. A method according to claim 1, comprising a step of introducing a second type of indicator ions into the analyzer region.

7. A method according to claim 6, wherein the first and second types of indicator ions are introduced into the analyzer region during a same overlapping period of time.

8. A method according to claim 6, wherein the first and second types of indicator ions are introduced into the analyzer region during first and second different periods of time, respectively.

9. A method according to claim 6, comprising a step of determining a compensation voltage for transmitting the second type of indicator ions through the analyzer region in the presence of the flow of a carrier gas and at a same given asymmetric waveform voltage.

10. A method according to claim 6, comprising a step of determining a compensation voltage for transmitting the second type of indicator ions through the analyzer region in the presence of the flow of a carrier gas and at a second different asymmetric waveform voltage.

11. A method according to claim 6, comprising a step of verifying a determined amount of the vapour that is present in the carrier gas in dependence upon a first result obtained using the first type of indicator ions and a second result obtained using the second type of indicator ions.

12. A method according to claim 6, comprising the steps of:
    determining an amount of the vapour that is present in the carrier gas based upon a result of the step of comparing using the first type of indicator ion;
    determining an amount of the vapour that is present in the carrier gas based upon a result of a step of comparing using the second type of indicator ion; and,
    verifying the amount of the vapour that is present in the carrier gas in dependence upon a first result obtained using the first type of indicator ions and a second result obtained using the second type of indicator ions.

13. A method of detecting trace levels of a vapour in a carrier gas, comprising the steps of:
    providing a flow of a carrier gas through an analyzer region of a high field asymmetric waveform ion mobility spectrometer, the carrier gas including a trace amount of a vapour of a compound of interest;
    introducing indicator ions into the analyzer region;
    transmitting the indicator ions through the analyzer region at a given combination of an asymmetric waveform voltage and a compensation voltage; and,
    determining a value relating to a concentration of the vapour based upon a comparison of the compensation voltage for transmitting the indicator ions, to calibration data relating to compensation voltage values for transmitting the indicator ions at a same asymmetric waveform voltage for each of a plurality of different known amounts of the vapour,
    whereby the vapour of the compound of interest is substantially other than ionized.

14. A method according to claim 13, wherein the compound of interest is other than water.

15. A method according to claim 13, wherein the step of transmitting includes a step of varying the compensation voltage applied to an electrode of the analyzer region whilst applying a same asymmetric waveform voltage so as to obtain a compensation voltage spectrum for the indicator ions in the presence of the vapour.

16. A method according to claim 13, wherein the carrier gas comprises a purified first gas in addition to the vapour.

17. A method according to claim 13, wherein the carrier gas comprises a mixture of two or more gases in addition to the vapour.

18. A method according to claim 17, wherein the carrier gas comprises substantially air in addition to the vapour.

19. A method according to claim 13, wherein the step of introducing indicator ions into the analyzer region includes a step of selecting a suitable type of ion for use as the indicator ion.

20. A method according to claim 15, wherein the step of introducing indicator ions into the analyzer region includes a step of selecting a suitable type of ion for use as the indicator ion.

21. A method according to claim 19, wherein the suitable type of ion is selected on the basis of an observed change, as a function of the amount of the vapour that is present in the carrier gas, of at least one of the CV for transmitting the type of ion and a separation parameter relating to the type of ion.

22. A method according to claim 21, wherein the separation parameter relates to the shape of a peak in the compensation voltage spectrum arising from the type of ion.

23. A method according to claim 21, wherein the separation parameter relates to the separation of peaks in the compensation voltage spectrum arising from the type of ion.

24. An apparatus for detecting trace levels of a vapour in a carrier gas comprising:
 a gas source for providing a flow of a carrier gas including a trace amount of a vapour of interest;
 an analyzer region defined by a space between two spaced-apart electrodes, the analyzer region having an inlet at a first end and an outlet at a second end for providing, in use, a flow of the carrier gas including a trace amount of the vapour of interest through the analyzer region;
 an ionization source disposed adjacent to the inlet of the analyzer region for producing indicator ions from at least a sample containing indicator ion precursors and for introducing the indicator ions through the inlet and into the analyzer region; and,
 a power supply connectable to at least one of the two electrodes and capable of applying an asymmetric waveform voltage to the at least one of the two electrodes and a direct-current compensation voltage to the at least one of the two electrodes, to selectively transmit the indicator ions through the analyzer region at a given combination of asymmetric waveform voltage and compensation voltage.

25. An apparatus according to claim 24, wherein the carrier gas is other than air.

26. An apparatus according to claim 24, comprising a source of the at least a sample containing indicator ion precursors in communication with the ionization source, for providing the at least a sample containing indicator ion precursors to the ionization source.

27. An apparatus according to claim 24, comprising a detector in fluid communication with the outlet for detecting indicator ions extracted from the analyzer region through the outlet.

28. An apparatus according to claim 27, wherein the power supply is adapted to vary the compensation voltage applied to the at least one of the two electrodes as a function of time, so as to produce a compensation voltage spectrum for the indicator ions.

29. An apparatus according to claim 28, comprising a processor in electrical communication with the detector for receiving a signal therefrom, the signal including information relating to a number of the indicator ions that are selectively transmitted through the analyzer region at a given compensation voltage value and in the presence of the carrier gas.

30. An apparatus according to claim 29, including a memory in electrical communication with the processor having calibration data stored therein, the calibration data relating to compensation voltage values for transmitting the indicator ions through the analyzer region at a same asymmetric waveform voltage for each of a plurality of different known amounts of the vapour of interest.

31. An apparatus according to claim 27, wherein the detector is selected from a group comprising: a mass spectrometer and an electrometric detector.

32. An apparatus according to claim 24, wherein the gas source comprises a probe in fluid communication with the inlet of the analyzer region for sampling an atmosphere external to the analyzer region and for providing the sampled atmosphere as at least a portion of the flow of the carrier gas including a trace amount of the vapour of interest through the analyzer region.

33. An apparatus according to claim 26, wherein the at least a sample containing indicator ion precursors comprises a first sample containing first indicator ion precursors for producing a flow of first indicator ions and a second sample containing second indicator ion precursors for producing a flow of second indicator ions.

34. An apparatus according to claim 26, wherein the at least a sample containing indicator ion precursors comprises a sample containing first indicator ion precursors and second indicator ion precursors for providing a flow of first and second indicator ions.

35. An apparatus according to claim 26, comprising a second ionization source in fluid communication with the inlet of the analyzer region for producing a flow of second indicator ions from at least a second sample containing indicator ion precursors and for introducing the flow of second indicator ions through the inlet and into the analyzer region.

36. An apparatus according to claim 35, wherein the ionization source and the second ionization source are adapted to operate during a same overlapping period of time so as to provide a flow of ions including the flow of indicator ions and the flow of second indicator ions through the inlet and into the analyzer region.

37. An apparatus according to claim 24, wherein the two electrodes comprise outer and inner generally cylindrical coaxially aligned electrodes defining a generally annular space therebetween, the annular space forming the analyzer region.

38. An apparatus according to claim 24, wherein the two electrodes are planar.

39. A computer readable storage medium having stored therein data relating to instructions for performing the steps of:
 receiving a first feedback signal from a FAIMS apparatus, the first feedback signal relating to a compensation voltage value for transmitting a first type of indicator ions through the analyzer region of a FAIMS in the presence of an unknown amount of a vapour of interest and at a given applied asymmetric waveform voltage;
 receiving calibration data from a memory, the calibration data including a compensation voltage value for transmitting the first type of indicator ions through the analyzer region of a FAIMS in the presence of each one of a plurality of different known amounts of the vapour of interest and at the given applied asymmetric waveform voltage; and, in dependence upon the first feedback signal and the calibration data, determining a value relating to an amount of the unknown amount of the vapour of interest.

40. A computer readable storage medium according to claim 39, having stored therein data relating to instructions for performing the steps of:

providing a known amount of the vapour of interest through the analyzer region of the FAIMS at the given applied asymmetric waveform voltage;

providing the first type of indicator ions through the analyzer region of the FAIMS in the presence of the known amount of the vapour of interest;

varying the compensation voltage applied to the FAIMS to determine an optimal compensation voltage for transmitting the first type of indicator ions in the presence of the known amount of the vapour of interest and at the given applied asymmetric waveform voltage; and.

storing data in the memory, the data including information relating to the optimal compensation voltage for transmitting the first type of indicator ions in the presence of the known amount of the vapour of interest and at the given applied asymmetric waveform voltage.

41. A computer readable storage medium according to claim 40, having stored therein data relating to instructions for performing the step of repeating the steps of claim 40 for each of a plurality of different known amounts of the vapour of interest.

42. A computer readable storage medium according to claim 41, having stored therein data relating to instructions for performing the step of repeating the steps of claim 40 for a second type of indicator ion and for each of a plurality of different known amounts of the vapour of interest.

43. A computer readable storage medium according to claim 42, having stored therein data relating to instructions for performing the steps of:

repeating the steps of claim 39 using the second type of indicator ion; and comparing the value relating to an amount of the unknown amount of the vapour of interest determined using the first type of indicator ion and the value relating to an amount of the unknown amount of the vapour of interest determined using the second type of indicator ion; and, providing a trusted value relating to an amount of the unknown amount of the vapour of interest based upon a result of the comparison.

* * * * *